(12) United States Patent
Sumi et al.

(10) Patent No.: US 6,365,755 B1
(45) Date of Patent: Apr. 2, 2002

(54) AMMONIUM 3,5,6-TRIHYDROXYHEXANOATE DERIVATIVES AND PREPARATION PROCESS THEREOF

(75) Inventors: Kenzo Sumi; Toshiyuki Murayama; Yoshiharu Gonda; Hideki Nara; Takashi Moroi, all of Kanagawa (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 09/930,263

(22) Filed: Aug. 16, 2001

(30) Foreign Application Priority Data

Aug. 23, 2000 (JP) .............................. 12-252907

(51) Int. Cl.[7] .............................. C07D 319/06
(52) U.S. Cl. .................. 549/214; 549/369; 549/373; 549/374; 549/357
(58) Field of Search ................ 549/357, 369, 549/373, 374

(56) References Cited

U.S. PATENT DOCUMENTS

| | | | |
|---|---|---|---|
| 4,970,313 A | 11/1990 | Wess et al. | 544/335 |
| 4,977,279 A | 12/1990 | Wess et al. | 549/274 |
| 4,983,759 A | 1/1991 | Inoue et al. | 500/174 |
| 5,103,024 A | 4/1992 | Millar et al. | 549/373 |
| 5,278,313 A | 1/1994 | Thottathil et al. | 548/252 |
| 5,286,883 A | 2/1994 | Sakurai et al. | 549/420 |

FOREIGN PATENT DOCUMENTS

| | | | |
|---|---|---|---|
| DE | 41 28 345 C1 | 6/1993 | |
| EP | 0 374 922 | 6/1990 | |
| WO | 92/06968 | 4/1992 | ......... C07D/319/06 |

OTHER PUBLICATIONS

Gerhard Beck, Heiner Jendralla, and Kurt Kesseler, "Practical Large Scale Synthesis of tert–Butyl (3R, 5S)–6–Hydroxy–3,5–O–isopropylidene–3,5–dihydroxyhexanoate: Essential Building for HMG–CoA Reductase Inhibitors", Synthesis, p 1014–1018 (1995).

*Primary Examiner*—Floyd D. Higel
*Assistant Examiner*—Golam M. M. Shameem
(74) *Attorney, Agent, or Firm*—Sughrue Mion, PLLC

(57) ABSTRACT

Provided are a novel ammonium (3R,5S)-3,5,6-trihydroxyhexanoate derivative represented by the following formula (I):

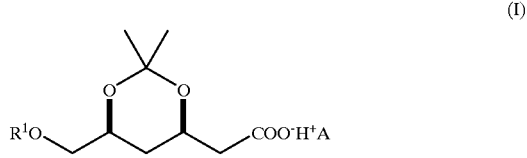

(I)

wherein $R^1$ represents a benzyl group which may have a substituent, a triphenylmethyl group which may have a substituent, an organosilyl group or a $C_{1-5}$ acyl group; and A means a specific amine; and a preparation process of the derivative.

4 Claims, No Drawings

AMMONIUM 3,5,6-TRIHYDROXYHEXANOATE DERIVATIVES AND PREPARATION PROCESS THEREOF

FIELD OF THE INVENTION

The present invention relates to an ammonium (3R,5S)-3,5,6-trihydroxyhexanoate derivative which is a novel useful compound as an intermediate for the synthesis of pharmaceuticals.

This ammonium (3R,5S)-3,5,6-trihydroxyhexanoate derivative is a useful compound as an intermediate commonly used for the synthesis of various HMG-CoA (3-hydroxyglutaryl coenzyme A) reductase inhibitors whose action as an anti-hyperlipemia has attracted attentions.

BACKGROUND OF THE INVENTION

As a process for preparing a (3R,5S)-3,5,6-trihydroxyhexanoic acid derivative, already reported are (1) a process for diastereoseletively reducing an (S)-5,6-dihydroxy-3-oxohexanoic acid derivative with a reducing agent such as sodium borohydride and, trialkylborane or alkoxydialkylborane (JP-A-1-199945 (the term "JP-A" as used herein means an "unexamined published Japanese patent application"), JP-A-2-262537); and (2) a process for subjecting an (S)-5,6-dihydroxy-3-oxohexanoic acid derivative to asymmetric hydrogenation in the presence of a ruthenium-optically active phosphine complex as a catalyst (JP-A-6-65226).

Many of the (3R,5S)-3,5,6-trihydroxyhexanoic acid derivatives so far reported are obtained as oily matter. It is the present situation that such crude products tend to be provided for a subsequent step without being improved into a high-purity syn-isomer.

According to the report by G. Beck, et al. (Synthesis, 1014(1995)), the below-described compound (a) is oily matter, from which a crude product (b) is obtained as oily matter by isolating and purifying the oily matter (a) by chromatography on a silica gel column, followed by reductive debenzylation. Chromatography on a silica gel column, however, is not suited for production on an industrial scale.

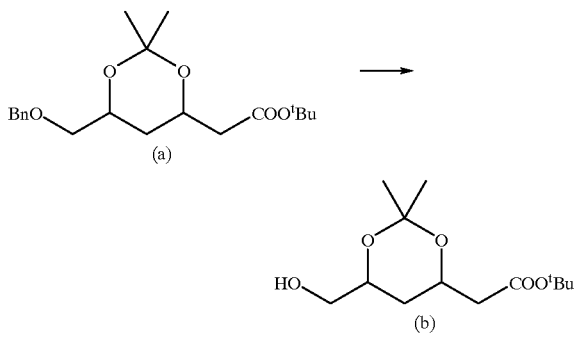

wherein Bn means a benzyl group and $^t$Bu means a tert-butyl group.

For preparation of various HMG-CoA reductase inhibitors, tert-butyl (3R,5S)-3,5-O-isopropylidene-3,5,6-trihydroxyhexanoate (b) having the 6-hydroxyl group deprotected is a particularly important compound, because the 6-position of the (3R,5S)-3,5,6-trihydroxyhexanoic acid derivative is a bonding site to another compound.

In consideration of the preparation on an industrial scale, it is preferred to isolate and purify the compound formed in each step as highly pure and stable crystals which can be handled easily.

Although reports on the isolation of a (3R,5S)-3,5,6-trihydroxyhexanoic acid derivative in the form of crystals are not so many, examples include: 1) U.S. Pat. No. 5,278,313 describes preparation of compounds (c) and (e), which will be described below, in the form of crystals at −20 to −5° C. It does not include a description on diastereoselectivity. Moreover, no attempt is made to improve the diastereoselectivity by recrystallization. 2) JP-A-2-262537 describes preparation of the below-described compounds (c) and (d) in the form of crystals by isolation and purification through chromatography on a silica gel column. As described above, however, separation by chromatography on a silica gel column is not suited for industrial production. 3) JP-T-6-502162 (the term "JP-T" as used herein means an "unexamined published Japanese patent application based on International application") describes isolation of the below-described compound (f) (X=Cl, Br or NO$_2$) as a solid. No attempt, however, is made in order to improve the diastereoselectivity by crystallization.

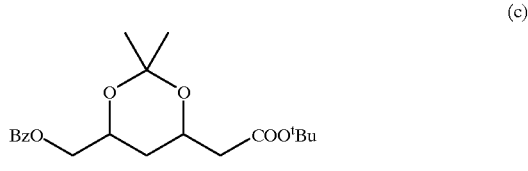

(c)

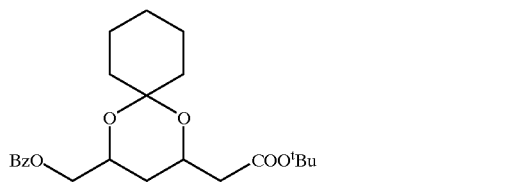

(d)

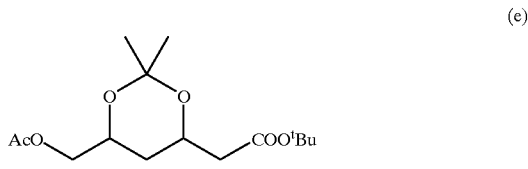

(e)

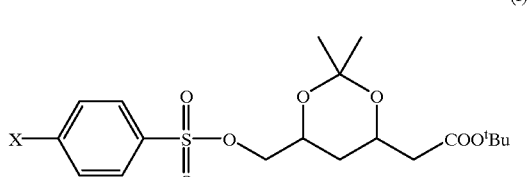

(f)

wherein Bz represents a benzoyl group, $^t$Bu means a tert-butyl group, Ac means an acetyl group and X represents a chlorine atom, a bromine atom or a nitro group.

Although it is essential to improve the diastereoselectivity of a (3R,5S)-3,5,6-trihydroxyhexanoic acid derivative for production on an industrial scale, it is the present state that no attempt has been made to improve the diastereoselectivity by crystallization.

SUMMARY OF THE INVENTION

An object of the present invention is therefore to prepare, safely in a high yield in a simple manner, a (3R,5S)-3,5,6-trihydroxyhexanoic acid derivative which can satisfy the above-described demands, is in the form of crystals permitting easy handling and has high chemical purity.

Under such situations, the present inventors have carried out an extensive investigation with a view to attaining the above-described object. As a result, it has been found that a novel ammonium (3R,5S)-3,5,6-trihydroxyhexanoate derivative in the form of crystals can be prepared in a high yield by causing a specific amine to act on a (3R,5S)-3,5,6-trihydroxyhexanoic acid derivative. It has also been found that isolation and purification of an ammonium derivative in the form of crystals permitting easy handling make it possible to improve the chemical purity of the derivative and that the chemical purity thus attained is markedly high, leading to the completion of the present invention.

The present invention therefore embraces the following aspects.

1) An ammonium (3R,5S)-3,5,6-trihydroxyhexanoate derivative represented by the following formula (I):

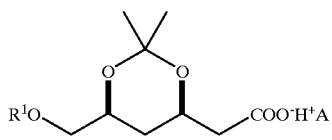

(I)

wherein $R^1$ represents a benzyl group which may have a substituent, a triphenylmethyl group which may have a substituent, an organosilyl group or a $C_{1-5}$ acyl group; and A represents at least one amine selected from the group consisting of a primary amine represented by the following formula (IIIa):

(IIIa)

(in which $R^2$ represents a $C_{1-7}$ alkyl group or a $C_{5-7}$ alicyclic group), a primary benzylamine represented by the following formula (IIIb):

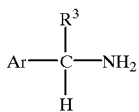

(IIIb)

(in which $R^3$ represents a hydrogen atom, a methyl group or a hydroxymethyl group and Ar represents a phenyl group which may have a substituent), a secondary amine represented by the following formula (IIIc):

(IIIc)

(in which $R^4$ and $R^5$ are the same or different and each independently represents a $C_{5-7}$ alicyclic group), cinchamidine, cinchotine, cinchonamine, cinchonidine and cinchonine.

2) An ammonium (3R,5S)-3,5,6-trihydroxyhexanoate as described above in 1), wherein a ratio of the syn-isomer to the anti-isomer falls within a range of 99.0/1.0 to 100/0.

3) A process for producing an ammonium (3R,5S)-3,5,6-trihydroxyhexanoate in the form of crystals, which comprises causing the amine (A) as described above in 1) to act on a (3R,5S)-3,5,6-trihydroxyhexanoic acid represented by the following formula (II):

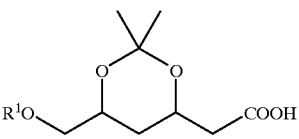

(II)

wherein $R^1$ has the same meaning as described above.

4) A process for producing a high-purity ammonium (3R,5S)-3,5,6-trihydroxyhexanoate in the form of crystals, which comprises causing the amine (A) as described above in 1) to act on the (3R,5S)-3,5,6-trihydroxyhexanoic acid represented by the formula (II) and crystallizing the resulting ammonium (3R,5S)-3,5,6-trihydroxyhexanoate derivative precursor to improve the chemical purity thereof.

DETAILED DESCRIPTION OF THE INVENTION

The present invention will next be described more specifically.

In the ammonium (3R,5S)-3,5,6-trihydroxyhexanoate derivative of the invention, $R^1$ represents a benzyl group which may have a substituent, a triphenylmethyl group which may have a substituent, an organosilyl group or a $C_{1-5}$ acyl group.

Specific examples of $R^1$ include a benzyl group which may have a substituent, for example, a lower $C_{1-4}$ alkyl group such as methyl, ethyl, propyl, isopropyl, n-butyl, tert-butyl, isobutyl or sec-butyl, a lower $C_{1-4}$ alkoxy group such as methoxy, ethoxy, propoxy or butoxy, or a halogen atom such as fluorine, chlorine, bromine or iodine; a triphenylmethyl group which may have a substituent, for example, a lower $C_{1-4}$ alkyl group such as methyl, ethyl, propyl, isopropyl, n-butyl, tert-butyl, isobutyl or sec-butyl, a lower $C_{1-4}$ alkoxy group such as methoxy, ethoxy, propoxy or butoxy, or a halogen atom such as fluorine, chlorine, bromine or iodine; organosilyl groups such as tert-butyldimethylsilyl, tert-butyldiphenylsilyl, triethylsilyl, dimethylcumylsilyl, triisopropylsilyl, dimethylthexylsilyl, trimethylsilyl, and dimethylhexylsilyl; $C_{1-5}$ acyl groups such as formyl, acetyl, propionyl, butyloyl, valeloyl, isovaleloyl and pivaloyl.

Preferred specific examples of $R^1$ include benzyl, triphenylmethyl, tert-butyldimethylsilyl and acetyl groups.

In the ammonium (3R,5S)-3,5,6-trihydroxyhexanoate derivative (I) of the invention, A represents an amine.

The amine (A) is at least one amine selected from the amines represented by the above-described formulas (IIIa), (IIIb) and (IIIc), cinchamidine, cinchotine, cinchonamine, cinchonidine and cinchonine.

Specific examples of $R^2$ in the formula (IIIa) include $C_{1-7}$ alkyl groups such as methyl, ethyl, propyl, isopropyl, n-butyl, tert-butyl, isobutyl, sec-butyl, pentyl, hexyl and heptyl; and $C_{5-7}$ alicyclic groups such as cyclopentyl, cyclohexyl and cycloheptyl.

Specific examples of Ar in the formula (IIIb) include phenyl groups which may have a substituent such as phenyl, p-tolyl and xylyl.

Specific examples of $R^4$ or $R^5$ in the formula (IIIc) include $C_{5-7}$ alicyclic groups such as cyclopentyl, cyclohexyl and cycloheptyl.

Specific preferred examples of the amine (A) are as follows: primary amines of the formula (IIIa), for example, alkyl-containing primary amines such as propylamine and tert-butylamine, and alicyclic primary amines such as cyclohexylamine; primary amines of the formula (IIIb), for example, benzyl-containing primary amines such as benzylamine, phenylethylamine and phenylethanolamine; secondary amines of the formula (IIIc), for example, alicyclic secondary amines such as dicyclohexylamine; cinchonidine; and cinchonine. More preferred are primary amines such as propylamine, tert-butylamine, cyclohexylamine, benzylamine, phenylethylamine and phenylethanolamine.

The ammonium (3R,5S)-3,5,6-trihydroxyhexanoate derivative of the invention is prepared in accordance with the following reaction.

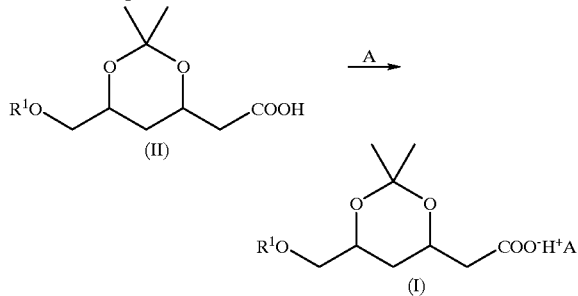

wherein $R^1$ represents a benzyl group which may have a substituent, a triphenylmethyl group which may have a substituent, an organosilyl group or a $C_{1-5}$ acyl group and A means an amine.

The ammonium (3R,5S)-3,5,6-trihydroxyhexanoate derivative (I) is prepared in the form of crystals by causing the above-described amine (A) to act on (3R, 5S)-3,5,6-trihydroxyhexanoic acid (II) as a starting material and then, cooling the reaction product.

The (3R,5S)-3,5,6-trihydroxyhexanoic acid (II) to be used in the invention is available by a known manner, for example, that described in JP-A-2-289537 or JP-A-6-65226.

The amine (A) is used in an amount of 1 to 2 times, more preferably 1 to 1.3 times the mole relative to 1 mole of the (3R,5S)-3,5,6-trihydroxyhexanoic acid (II).

As a reaction solvent, usable are those which do not adversely affect the reaction. Examples include esters such as methyl acetate, ethyl acetate, propyl acetate and butyl acetate; aromatic hydrocarbons such as benzene, toluene and xylene; ethers such as diethyl ether, diisopropyl ether, dimethoxyethane, tetrahydrofuran, dioxane and 1,3-dioxolan; ketones such as acetone, methyl ethyl ketone, diethyl ketone, methyl isobutyl ketone and cyclohexanone; alcohols such as methanol, ethanol, isopropyl alcohol and butanol; acetonitrile; and water; and mixed solvents thereof.

The above-exemplified solvent is usually employed in an amount of 1 to 100 times the volume, preferably 1 to 50 times the volume, of the mass (or volume) of the (3R,5S)-3,5,6-trihydroxyhexanoic acid (II).

This reaction is usually conducted in an inert gas atmosphere such as nitrogen gas or argon gas. This reaction is usually conducted for about 30 minutes to 10 hours at a temperature of about 20 to 50° C. By subsequent stirring at about −20 to 50° C. for 1 to 10 hours, reaction is terminated, whereby an ammonium (3R,5S)-3,5,6-trihydroxyhexanoate derivative (I) can be obtained as crystals. The above-described conditions can be changed as needed, depending on the kind of the amine (A) to be employed.

The ammonium (3R,5S)-3,5,6-trihydroxyhexanoate derivative (I) of the present invention thus prepared is in the form of crystals as is apparent from Examples which will be described later. Crystallization makes it possible to prepare the derivative at a high selectivity to the syn-isomer [(3R, 5S)-isomer] relative to the anti-isomer and even if the preparation ratio of the syn-isomer is insufficient, high-purity syn-isomer [(3R,5S)-isomer] is available by recrystallization. In the invention, a ratio of the syn-isomer to the anti-isomer ranging from 99.0/1.0 to 100/0, preferably 99.1/0.9 to 100/0, more preferably 99.4/0.6 to 100/0 can be attained. Moreover, since the derivative of the present invention is obtained in the form of crystals, it has stability by far superior to that in the oily form.

In consideration of the difficulty in purification of the (3R,5S)-3,5,6-trihydroxyhexanoic acid derivative in the industrial preparation process, the invention, which facilitates the purification by preparing its ammonium salt derivative (I) in the form of crystals, brings about a large merit in the synthesis research of an HMG-CoA reductase inhibitor.

EXAMPLES

The present invention will hereinafter be described in detail by examples. It should however be borne in mind that the present invention is not limited to or by them.

In the examples, the following apparatuses were employed for the measurement of physical properties.

Nuclear magnetic resonance spectrum ($^1$H-NMR): "Gemini-2000" (200 MHz) (trade name; product of Varian, Inc.)

Internal standard: tetramethylsilane (TMS), sodium 2,2-dimethyl-2-silapentane-5-sulfonate (DSS)

Melting point: "MP-S3" (trade name; product of Yanagimoto Shoji Co., Ltd.)

Gas chromatography (GLC): "HP5890 SERIES II" (trade name; product of Hewlett Packard)

High-performance liquid chromatography (HPLC): "Hitachi L-600" (trade name; product of Hitachi, Ltd.)

Synthesis Example 1

Synthesis of (3R,5S)-6-benzyloxy-3,5-O-isopropylidene-3,5-dihydroxyhexanoic acid (2)

(1) Synthesis of methyl (3R,5S)-6-benzyloxy-3,5-O-isopropylidene-3,5-dihydroxyhexanoate (1)

In a similar manner to Reference Example 4 and Example 1 of JP-A-6-65226 except for the use of methyl potassium malonate instead of the ethyl potassium malonate of Reference Example 4 of JP-A-6-65226, the target methyl (3R, 5S)-6-benzyloxy-3,5-O-isopropylidene-3,5-dihydroxyhexanoate (1) was obtained as colorless oil. As a result of gas chromatography analysis, the syn-isomer/anti-isomer ratio of the product was found to be 95.3/4.7.

$^1$H-NMR (δ ppm, J Hz, CDCl$_3$): 7.34–7.29(m,5H), 4.57 (d,2H,J=1.50), 4.39–4.27(m,1H), 4.18–4.06(m,1H), 3.68(s, 3H), 3.50(dd,1H,J=5.60,10.0), 3.37(dd,1H,J=5.00,10.0), 2.56(dd,1H,J=7.02,15.6), 2.38(dd,1H,J=5.80,15.6), 1.63(dt, 1H,J=2.4,12.6), 1.47(s,3H), 1.39(s,3H), 1.26(dt,1H,J=9.00, 12.6).

GLC analysis

Column: Chirasil-Dex CB 0.25 mm×25 m (CHROMPACK)

Injection temperature: 200° C.

Column temperature: fixed at 170° C.

Detection temperature: 250° C.

(2) Synthesis of (3R,5S)-6-benzyloxy-3,5-O-isopropylidene-3,5-dihydroxyhexanoic acid (2)

To a solution of 238.1 g (0.772 mol) of methyl (3R,5S)-6-benzyloxy-3,5-O-isopropylidene-3,5-dihydroxyhexanoate (1) in methanol (475 ml), added dropwise at 13° C. was 324.0 g (0.811 mol) of a 10% aqueous sodium hydroxide solution. After 5 hours, the solvent was distilled under reduced pressure. Water (360 ml) was added to the residue, followed by washing with butyl acetate. After addition of 365 ml of a 2M aqueous hydrochloric acid solution to the water layer, the resulting mixture was extracted twice with 480 ml of toluene and then washed with 360 ml of water. The toluene layer was concentrated under reduced pressure, whereby 214.1 g (yield: 94.2%) of crude (3R,5S)-6-benzyloxy-3,5-O-isopropylidene-3,5-dihydroxyhexanoic acid (2) was obtained as colorless oil.

$^1$H-NMR (δ ppm, J Hz, CDCl$_3$): 7.36–7.26(m,5H), 4.59 (d,1H,J=12.2), 4.54(d,1H,J=12.2), 4.35–4.30(m,1H), 4.15–4.10(m,1H), 3.51(dd,1H,J=5.7,10.0), 3.39(dd,1H,J=4.8,10.0), 2.57(dd,1H,J=7.2,15.9), 2.47(dd,1H,J=5.4,15.9), 1.65(dt,1H,J=2.5,12.8), 1.48(s,3H), 1.41(s,3H), 1.30(dt,1H, J=11.7,12.8).

Synthesis Example 2

Synthesis of (3R,5S)-6-triphenylmethyloxy-3,5-O-isopropylidene-3,5-dihydroxyhexanoic acid (5a)

(1) Synthesis of methyl (3R,5S)-3,5-O-isopropylidene-3,5,6-trihydroxyhexanoate (3)

In a 200 ml autoclave were charged 30.0 g (98.8 mmol) of the methyl (3R,5S)-6-benzyloxy-3,5-O-isopropylidene-3,5-dihydroxyhexanoate (1) obtained in Synthesis Example 1(1), 1.5 g of 10% palladium-carbon and 60 ml of methanol. After purging with nitrogen, hydrogen was charged at 3 MPa. The mixture was then stirred at 35° C. for 6 hours. Disappearance of the raw material was confirmed by gas chromatography analysis. After filtration, the filtrate was concentrated, whereby 20.9 g (95.8 mmol) of methyl (3R,5S)-3,5-O-isopropylidene-3,5,6-trihydroxyhexanoate (3) was obtained as colorless oil.

$^1$H-NMR (δ Hz, J Hz, CDCl$_3$): 4.43–4.27(m,1H), 4.09–3.95(m,1H), 3.68(s,3H), 3.61(dd,1H,J=2.80,11.2), 3.49(dd,1H,J=6.00,11.2), 2.56(dd,1H,J=7.00,15.6), 2.38(dd,1H,J=6.20,15.6), 1.51(dt,1H,J=2.40,12.6), 1.47(s,3H), 1.38 (s,3H), 1.29(dt,1H,J=9.00,12.6).

(2) Synthesis of methyl (3R,5S)-6-triphenylmethyloxy-3,5-O-isopropylidene-3,5-dihydroxyhexanoate (4a)

A 100 ml egg-plant type flask were charged with 4.00 g (18.3 mmol) of methyl (3R,5S)- 3,5-O-isopropylidene-3,5,6-trihydroxyhexanoate (3), 5.62 g (20.2 mmol) of trityl chloride, 224 mg (1.83 mmol) of 4-dimethylaminopyridine, 2.23 g (22.0 mmol) of triethylamine and 40 ml of methylene chloride. The resulting mixture was stirred overnight at room temperature. After confirming the completion of the reaction by thin-layer chromatography (which will hereinafter be abbreviated as "TLC"), the reaction mixture was concentrated. By chromatography on a silica gel column (solvent: hexane/ethyl acetate=5/1), 4.68 g (10.2 mmol) of the target methyl (3R,5S)-6-triphenylmethylxoxy-3,5-O-isopropylidene-3,5-dihydroxyhexanoate (4a) was obtained as colorless oil.

$^1$H-NMR (δ ppm, J Hz, CDCl$_3$): 7.46–7.43(m,6H), 7.30–7.21(m,9H), 4.35–4.30(m,1H), 4.06–4.02(m,1H), 3.69 (s,3H), 3.23(dd,1H,J=5.4,9.3), 2.97(dd,1H,J=5.7,9.3), 2.54 (dd,1H,J=7.2,15.5), 2.40(dd,1H,J=5.7,15.5), 1.69(dt,1H,J= 2.5,12.8), 1.46(s,3H), 1.37(s,3H), 1.27–1.18(m,1H).

(3) Synthesis of (3R,5S)-6-triphenylmethyloxy-3,5-O-isopropylidene-3,5-dihydroxyhexanoic acid (5a)

A 100 ml egg-plant type flask was charged with 2.80 g (6.08 mmol) of methyl (3R,5S)-6-triphenylmethyloxy-3,5-O-isopropylidene-3,5-dihydroxyhexanoate (4a) and 30 ml of ethanol. The resulting mixture was cooled to 10° C. After dropwise addition of 2.43 g (6.08 mmol) of a 10% aqueous solution of sodium hydroxide, 50 ml of water was charged further. The resulting mixture was stirred overnight at room temperature and then stirred at 35° C. After concentration, the residue was added with a 5% aqueous hydrochloric acid solution until the pH became 3, followed by extraction with toluene. The oil layer thus obtained was washed twice with 100 ml of water, concentrated and then dried in a high vacuum, whereby 2.07 g (4.64 mmol) of the target (3R,5S)-6-triphenylmethyloxy-3,5-O-isopropylidene-3,5-dihydroxyhexanoic acid (5a) was obtained as colorless oil.

$^1$H-NMR (δ ppm, J Hz, CDCl$_3$): 7.45–7.43(m,6H), 7.31–7.22(m,9H), 4.32–4.30(m,1H), 4.05–4.02(m,1H), 3.25 (dd,1H,J=5.4,9.4), 2.99(dd,1H,J=5.8,9.4), 2.56–2.54(m,2H), 1.71(dt,1H,J=2.5,12.9), 1.48(s,3H), 1.42(s,3H), 1.28(.dt,1H, J=11.8,12.8).

Synthesis Example 3

Synthesis of (3R,5S)-6-tert-butyldimethylsilyloxy-3,5-O-isopropylidene-3,5-dihydroxyhexanoic acid (5b)

(1) Synthesis of methyl (3R,5S)-6-tert-butyldimethylsilyloxy-3,5-O-isopropylidene-3,5-dihydroxyhexanoate (4b)

A 100 ml egg-plant type flask were charged with 6.47 g (29.6 mmol) of the methyl (3R,5S)-3,5-O-isopropylidene-3,5,6-trihydroxyhexanoate (3) obtained in Synthesis Example 2(1), 4.04 g (59.3 mmol) of imidazole and 65 ml of methylene chloride, followed by dropwise addition of 9.83 g (32.6 mmol) of a 50% solution of tert-butyldimethylsilyl chloride in ethyl acetate at room temperature. The completion of the reaction was confirmed by TLC 1.5 hours after the dropwise addition. A 5% aqueous hydrochloric acid solution was then added until the pH became 6. The reaction mixture was extracted with methylene chloride. The oil layer thus obtained was washed twice with 100 ml of water and concentrated, whereby 9.45 g (28.4 mmol) of methyl (3R,5S)-6-tert-butyldimethylsilyloxy-3,5-O-isopropylidene-3,5-dihydroxyhexanoate (4b) was obtained as colorless oil.

1H-NMR (δ ppm, J Hz, CDCl$_3$): 4.32–4.29(m,1H), 3.94–3.87(m,1H), 3.65(s,3H), 3.64–3.42(m,2H), 2.53(dd, 1H,J=7.0,15.5), 2.37(dd,1H,J=5.9,15.5), 1.63(dt,1H,J=2.4, 12.7), 1.42(s,3H), 1.35(s,3H), 1.12(dt,1H,J=11.7,12.5), 0.85 (s,9H), 0.02(s,6H).

(2) Synthesis of (3R,5S)-6-tert-butyldimethylsilyloxy-3,5-O-isopropylidene-3,5-dihydroxyhexanoic acid (5b)

A 100 ml egg-plant type flask was charged with 9.45 g (28.4 mmol) of methyl (3R,5S)-6-tert-butyldimethylsilyloxy-3,5-O-isopropylidene-3,5-dihydroxyhexanoate (4b) and 20 ml of methanol, followed by cooling to 10° C. To the reaction mixture was added dropwise 13.1 g (32.8 mmol) of a 10% aqueous sodium hydroxide solution. The mixture was stirred overnight at room temperature. After concentration, the residue was washed twice with 200 ml of butyl acetate. A 5% aqueous solution of hydrochloric acid was added to the resulting water layer until the pH became 4, followed by extraction twice with 100 ml of toluene. The oil layer thus obtained was washed twice with 200 ml of water and concentrated, whereby 5.50 g (17.3 mmol) of the target (3R,5S)-6-tert-butyldimethylsilyloxy-3,5-O-isopropylidene-3,5-dihydroxyhexanoic acid (5b) was obtained as colorless oil.

$^1$H-NMR (δ ppm, J Hz, CDCl$_3$): 4.36–4.30(m,1H), 3.95–3.90(m,1H), 3.64(dd,1H,J=5.3,10.3), 3.46(dd,1H,J= 5.9,10.3), 2.38(dd,1H,J=6.8,14.9), 2.24(dd,1H,J=6.1,14.9), 1.73(dt,1H,J=2.4,12.7), 1.43(s,3H), 1.33(s,3H), 1.12(dt,1H, J=11.7,12.5), 0.87(s,9H), 0.04(s,6H).

Synthesis Example 4

Synthesis of (3R,5S)-6-acetoxy-3,5-O-isopropylidene-3,5-dihydroxyhexanoic acid (9)

(1) Synthesis of benzyl (3R,5S)-6-tert-butyldimethylsilyloxy-3,5-O-isopropylidene-3,5-dihydroxyhexanoate (6)

A 100 ml egg-plant type flask was charged with 8.7 g (28.8 mmol) of the (3R,5S)-6-tert-butyldimethylsilyloxy-3, 5-O-isopropylidene-3,5-dihydroxyhexanoic acid (5b)

obtained in Synthesis Example 3, 7.1 g (34.6 mmol) of N,N'-dicyclohexyl carbodiimide, 0.9 g (7.4 mmol) of dimethylaminopyridine, 3.7 g (34.6 mmol) of benzyl alcohol and 50 ml of tetrahydrofuran (which will hereinafter be abbreviated as "THF"). The mixture was stirred overnight at room temperature. After concentration of the reaction mixture, the residue was subjected to chromatography on a silica gel column (solvent: hexane/ethyl acetate=10/1), whereby 7.6 g (19.4 mmol) of the target benzyl (3R,5S)-6-tert-butyldimethylsilyloxy-3,5-O-isopropylidene-3,5-dihydroxyhexanoate (6) was obtained as colorless oil.

$^1$H-NMR (δ ppm, J Hz, CDCl$_3$): 7.36–7.33(m,5H), 5.14 (d,2H,J=2.60), 4.43–4.27(m,1H), 4.00–3.83(m,1H), 3.65 (dd,1H,J=5.00,15.2), 3.46(dd,1H,J=3.40,15.2), 2.59(dd,1H, J=7.60,15.2), 2.45(dd,1H,J=5.60,15.2), 1.65(dt,1H,J=2.40, 12.6), 1.42(s,3H), 1.35(s,3H), 1.22(dt,1H,J=9.00,12.6), 0.88 (s,9H), 0.05(s,6H).

(2) Synthesis of benzyl (3R,5S)-3,5-O-isopropylidene-3,5,6-trihydroxyhexanoate (7)

A 100 ml egg-plant type flask was charged with 7.6 g (19.4 mmol) of benzyl (3R,5S)-6-tert-butyldimethylsilyloxy-3,5-O-isopropylidene-3,5-dihydroxyhexanoate (6) and 10 ml of THF. After cooling to 10° C., 34.0 ml of a 1M THF solution of tetrabutylammonium fluoride (TBAF) was added dropwise to the reaction mixture. The temperature was allowed to rise back to room temperature, at which stirring was conducted for 2 hours. To the reaction mixture was added 40 ml of a saturated solution of ammonium chloride to separate an oil layer. The water layer was then extracted with 20 ml of butyl acetate. The oil layers thus obtained were combined, washed with water and then concentrated, whereby 4.6 g (15.6 mmol) of the target benzyl (3R,5S)-3,5-O-isopropylidene-3,5,6-trihydroxyhexanoate (7) was obtained as colorless oil.

$^1$H-NMR (δ ppm, J Hz, CDCl$_3$): 7.36–7.34(m,5H), 5.14 (d,2H,J=2.20), 4.44–4.28(m,1H), 4.07–3.93(m,1H), 3.61 (dd,1H,J=2.80,11.2), 3.49(dd,1H,J=6.00,11.2), 2.60(dd,1H, J=7.4,17.6), 2.44(dd,1H,J=5.8,17.6), 1.50(dt,1H,J=2.4, 12.6), 1.43(s,3H), 1.37(s,3H), 1.15(dt,1H,J=9.00,12.6).

(3) Synthesis of benzyl (3R,5S)-6-acetoxy-3,5-O-isopropylidene-3,5-dihydroxyhexanoate (8)

A 100 ml egg-plant type flask was charged with 5.8 g (19.7 mmol) of benzyl (3R,5S)-3,5-O-isopropylidene-3,5,6-trihydroxyhexanoate (7) and 30 ml of pyridine. After cooling to 10° C., 3.6 g (34.9 mmol) of acetic anhydride was added dropwise. After completion of the dropwise addition, the temperature was allowed to rise back to room temperature, at which stirring was conducted for 6 hours. Water (10 ml) and 20 ml of toluene were charged and the mixture was stirred. The oil layer was then separated from the reaction mixture. The water layer was extracted with 20 ml of butyl acetate. To the oil layers combined, a 5% aqueous hydrochloric acid solution was added until the pH became 7, followed by separation. After washing with water, the oil layer was concentrated. The concentrate was purified by chromatography on a silica gel column (solvent: hexane/ethyl acetate=10/1), whereby 4.3 g of the target benzyl (3R,5S)-6-acetoxy-3,5-O-isopropylidene-3,5-dihydroxyhexanoate (8) was obtained as colorless oil.

$^1$H-NMR (δ ppm, J Hz, CDCl$_3$): 7.36–7.26(m,5H) 5.15 (d,2H,J=2.00), 4.44–4.38(m,1H), 4.18–4.00(m,3H), 2.71 (dd,1H,J=7.80,14.2), 2.45(dd,1H,J=5.80,14.2), 2.07(s,3H), 1.58(dt,1H,J=2.4,12.6), 1.43(s,3H), 1.38(s,3H), 1.29(dt,1H, J=9.00,12.6).

(4) Synthesis of (3R,5S)-6-acetoxy-3,5-O-isopropylidene-3,5-dihydroxyhexanoic acid (9)

A 100 ml autoclave was charged with 3.3 g (9.81 mmol) of benzyl (3R,5S)-6-acetoxy-3,5-O-isopropylidene-3,5-dihydroxyhexanoate (8), 1.0 g of 5% palladium-alumina and 15 ml of THF. After purging with nitrogen, hydrogen was charged at 0.1 MPa. Stirring was then conducted at room temperature for 2 hours. The reaction mixture was filtered and the filtrate was concentrated, whereby 2.4 g (9.71 mmol) of the target (3R,5S)-6-acetoxy-3,5-O-isopropylidene-3,5-dihydroxyhexanoic acid (9) was obtained as colorless oil.

$^1$H-NMR (δ ppm, J Hz, CDCl$_3$): 4.42–4.27(m,1H), 4.20–3.95(m,3H), 2.73(dd,1H,J=7.00,16.2), 2.49(dd,1H,J= 5.60,16.2), 2.09(s,3H), 1.62(dt,1H,J=2.60,12.6), 1.48(s,3H), 1.42(s,3H), 1.31(dt,1H,J=9.00,12.6).

Example 1

Synthesis of cyclohexylammoniumr (3R,5S)-6-benzyloxy-3,5-O-isopropylidene-3,5-dihydroxyhexanoate (10a)

A 1 liter four-necked flask was charged with 55.3 g (188 mmol) of the (3R,5S)-6-benzyloxy- 3,5-O-isopropylidene-3,5-dihydroxyhexanoic acid (2) (syn-isomer/anti-isomer= 95.3/4.7) obtained in Synthesis Example 1 and 165 ml of a mixed solvent (ethyl acetate/acetone/water=1/1/0.03). A solution of 18.6 g (188 mmol) of cyclohexylamine in ethyl acetate (55 ml) was added dropwise at 34° C. over 1 hour. After completion of the dropwise addition, the reaction mixture was cooled to 10° C. The reaction mixture was stirred for 1 hour and then filtered to isolate crystals. The resulting crystals were dried under reduced pressure, whereby 64.9 g (165 mmol) of the target cyclohexylammonium (3R,5S)-6-benzyloxy-3,5-O-isopropylidene-3,5-dihydroxyhexanoate (10a) was obtained as colorless crystals. The results are shown in Table 1.

Yield: 87.8%; Melting point: 70.4 to 71.2° C.; $^1$H-NMR (δ ppm, J Hz, CDCl$_3$): 7.28–7.18(m,5H), 4.52(d,1H,J=12.3), 4.46(d,1H,J=12.3), 4.23–4.21(m,1H), 4.04–4.01(m,1H), 3.40(dd,1H,J=5.9,10.0), 3.28(dd,1H,J=4.4,10.0), 2.80–2.78 (m,1H), 2.30(dd,1H,J=6.4,14.9), 2.13(dd,1H,J=6.6,14.9), 1.88(d,2H,J=11.5), 1.65(d,2H,J=13.0), 1.58–1.51(m,2H), 1.39(s,3H), 1.31(s,3H), 1.23–1.02(m,6H).

To a mixed solution of 100 mg of the resulting cyclohexylammonium (3R,5S)-6-benzyloxy-3,5-O-isopropylidene-3,5-dihydroxyhexanoate (10a) and toluene (2 ml), 0.25 ml of a 5% aqueous hydrochloric acid solution was added dropwise to make the amine free. A 2M hexane solution (0.13 ml) of trimethylsilyldiazomethane was added, whereby methyl (3R,5S)-6-benzyloxy-3,5-O-isopropylidene-3,5-dihydroxyhexanoate (1) was obtained. As a result of gas chromatography analysis, the syn-isomer/anti-isomer ratio was found to be 99.8/0.2.

GLC analysis

Column: Chirasil-Dex CB 0.25 mm×25 m (product of CHROMPACK)

Injection temperature: 200° C.

Column temperature: fixed at 170° C.

Detection temperature: 250° C.

Example 2

Synthesis of tert-butylammonium (3R,5S)-6-benzyloxy-3,5-O-isopropylidene-3,5-dihydroxyhexanoate (10b)

A 50 ml egg-plant type flask was charged with 750 mg (2.55 mmol) of the (3R,5S)-6-benzyloxy-3,5-O-isopropylidene-3,5-dihydroxyhexanoic acid (2) (syn-isomer/anti-isomer=95.3/4.7) obtained in Synthesis Example 1 and 4.0 ml of a mixed solvent (ethyl acetate/acetone/water=1/1/0.03). A solution of 219 mg (2.99 mmol) of tert-butylamine in a 2.0 ml of mixed solvent (ethyl acetate/acetone/water=1/1/0.03) was slowly added dropwise at 35° C. After completion of the dropwise addition, the reaction mixture was cooled to room temperature. The reaction mixture was stirred for 30 minutes and then filtered to isolate crystals. The resulting crystals were dried under reduced pressure, whereby 756 mg (2.06 mmol) of the target tert-butylammonium (3R,5S)-6-benzyloxy-3,5O-isopropylidene-3,5-dihydroxyhexanoate (10b) was obtained as colorless crystals. The results are shown in Table 1.

Yield: 80.8%; Melting point: 66.9 to 67.7° C.; $^1$H-NMR (δ ppm, J Hz, CDCl$_3$): 7.35–7.25(m,5H), 4.58(d,1H,J=12.2), 4.53(d,1H,J=12.2), 4.36–4.30(m,$_1$H), 4.13–4.08(m,1H), 3.49(dd,1H,J=5.9,10.0), 3.36(dd,1H,J=4.6,10.0), 2.38(dd,1H,J=6.8,15.0), 2.24(dd,1H,J=6.1,15.0), 1.65(dt,1H,J=2.5,12.8), 1.45(s,3H), 1.36(s,3H), 1.27(s,9H), 1.20(dt,1H,J=11.8,12.5).

To a mixed solution of 100 mg of the resulting tert-butylammonium (3R,5S)-6-benzyloxy-3,5-O-isopropylidene-3,5-dihydroxyhexanoate (10b) and toluene (2 ml), 0.28 ml of a 5% aqueous hydrochloric acid solution was added dropwise to make the amine free. A 2M hexane solution (0.14 ml) of trimethylsilyldiazomethane was added, whereby methyl (3R,5S)-6-benzyloxy- 3,5-O-isopropylidene-3,5-dihydroxyhexanoate (1) was obtained. As a result of gas chromatography analysis, the syn-isomer/anti-isomer ratio was found to be 99.4/0.6.

GLC analysis

Column: Chirasil-Dex CB 0.25 mm×25 m (product of CHROMPACK)

Injection temperature: 200° C.

Column temperature: fixed at 170° C.

Detection temperature: 250° C.

Example 3

Synthesis of n-propylammonium (3R,5S)-6-benzyloxy-3,5-O-isopropylidene-3,5-dihydroxyhexanoate (10c)

A 50 ml egg-plant type flask was charged with 750 mg (2.55 mmol) of the (3R,5S)-6-benzyloxy-3,5-O-isopropylidene-3,5-dihydroxyhexanoic acid (2) (syn-isomer/anti-isomer 95.3/4.7) obtained in Synthesis Example 1 and 8.0 ml of ethyl acetate. A solution of 195 mg (2.99 mmol) of n-propylamine in ethyl acetate (2.0 ml) was slowly added dropwise at 35° C. After completion of the dropwise addition, the reaction mixture was cooled to room temperature. The reaction mixture was stirred for 1 hour and then filtered to isolate crystals. The resulting crystals were dried under reduced pressure, whereby 556 mg (1.58 mmol) of the target n-propylammonium (3R,5S)-6-benzyloxy-3,5-O-isopropylidene-3,5-dihydroxyhexanoate (10c) was obtained as colorless crystals. The results are shown in Table 1.

Yield: 62.0%; Melting point: 60.2 to 61.1° C.; $^1$H-NMR (δ ppm, J Hz, CDCl$_3$): 7.26–7.19(m,5H) 4.52(d,1H,J=12.2), 4.46(d,1H,J=12.2), 4.24–4.19(m,1H), 4.06–4.01(m,1H), 3.42(dd,1H,J=5.8,10.0), 3.29(dd,1H,J=4.6,10.0), 2.66(t,2H,J=7.4), 2.29(dd,1H,J=6.8,14.9), 2.17(dd,1H,J=5.9,14.9), 1.57–1.49(m,3H), 1.39(s,3H), 1.31(s,3H), 1.14(dt,1H,J=11.7,12.7), 0.85(t,3H,J=7.4).

To a mixed solution of 100 mg of the resulting propylammonium (3R,5S)-6-benzyloxy-3,5-O-isopropylidene-3,5-dihydroxyhexanoate (10c) and toluene (2 ml), 0.28 ml of a 5% aqueous hydrochloric acid solution was added dropwise to make the amine free. A 2M hexane solution (0.14 ml) of trimethylsilyldiazomethane was added, whereby methyl (3R,5S)-6-benzyloxy-3,5-O-isopropylidene-3,5-dihydroxyhexanoate (1) was obtained. As a result of gas chromatography analysis, the syn-isomer/anti-isomer ratio was found to be 99.1/0.9.

GLC analysis

Column: Chirasil-Dex CB 0.25 mm×25 m (product of CHROMPACK)

Injection temperature: 200° C.

Column temperature: fixed at 170° C.

Detection temperature: 250° C.

Example 4

Synthesis of benzylammonium (3R,5S)-6-benzyloxy-3,5-O-isopropylidene-3,5-dihydroxyhexanoate (10d)

A 50 ml egg-plant type flask was charged with 750 mg (2.55 mmol) of the (3R,5S)-6-benzyloxy-3,5-O-isopropylidene-3,5-dihydroxyhexanoic acid (2) (syn-isomer/anti-isomer=95.3/4.7) obtained in Synthesis Example 1 and 13.0 ml of ethyl acetate. A solution of 321 mg (3.00 mmol) of benzylamine in ethyl acetate (2 ml) was slowly added dropwise at 35° C. After completion of the dropwise addition, the reaction mixture was cooled to room temperature. The reaction mixture was stirred for 30 minutes and then filtered to isolate crystals. The resulting crystals were dried under reduced pressure, whereby 657 mg (1.64 mmol) of the target benzylammonium (3R,5S)-6-benzyloxy-3,5-O-isopropylidene-3,5-dihydroxyhexanoate (10d) was obtained as colorless crystals. The results are shown in Table 1.

Yield: 64.3%; Melting point: 70.3 to 71.1° C.; $^1$H-NMR (δ ppm, J Hz, CDCl$_3$): 7.73(br,3H), 7.25–7.16(m,10H), 4.51(d,1H,J=12.2), 4.45(d,1H,J=12.2), 4.10–4.05(m,1H), 3.98–3.93(m,1H), 3.80(s,2H), 3.37(dd,1H,J=6.0,10.1), 3.25(dd,1H,J=4.5,10.1), 2.12(dd,1H,J=6.8,15.0), 1.97(dd,1H,J=5.8,15.0), 1.40(dt,1H,J=2.3,12.8), 1.33(s,3H), 1.28(s,3H), 1.02(dt,1H,J=11.8,12.4).

To a mixed solution of 100 mg of the resulting benzylammonium (3R,5S)-6-benzyloxy-3,5-O-isopropylidene-3,5-dihydroxyhexanoate (10d) and toluene (2 ml), 0.25 ml of a 5% aqueous hydrochloric acid solution was added dropwise to make the amine free. A 2M hexane solution (0.13 ml) of trimethylsilyldiazomethane was added, whereby methyl (3R,5S)-6-benzyloxy-3,5-O-isopropylidene-3,5-dihydroxyhexanoate (1) was obtained. As a result of gas chromatography analysis, the syn-isomer/anti-isomer ratio was found to be 99.0/1.0.

GLC analysis

Column: Chirasil-Dex CB 0.25 mm×25 m (product of CHROMPACK)

Injection temperature: 200° C.

Column temperature: fixed at 170° C.

Detection temperature: at 250° C.

Example 5

Synthesis of (S)-1-phenylethylammonium (3R,5S)-6-benzyloxy-3,5-O-isopropylidene-3,5-dihydroxyhexanoate (10e)

A 50 ml egg-plant type flask was charged with 750 mg (2.55 mmol) of the (3R,5S)-6-benzyloxy-3,5-O-isopropylidene-3,5-dihydroxyhexanoic acid (2) (syn-isomer/anti-isomer=95.3/4.7) obtained in Synthesis Example 1 and 5 ml of a mixed solvent (ethyl acetate/acetone/water=1/1/0.03). A solution of 382 mg (3.15 mmol) of (S)-1-phenylethylamine in 2 ml of a mixed solvent (ethyl acetate/acetone/water=1/1/0.03) was slowly added dropwise at 35° C. After completion of the dropwise addition, the reaction mixture was stirred for 1 hour at the same temperature and then filtered to isolate crystals. The resulting crystals were dried under reduced pressure, whereby 975 mg (2.35 mmol) of the target (S)-1-phenylethylammonium (3R,5S)-6-benzyloxy-3,5-O-isopropylidene-3,5-dihydroxyhexanoate (10e) was obtained as colorless crystals. The results are shown in Table 1.

Yield: 92.1%; Melting point: 69.4 to 70.1° C.; $^1$H-NMR (δ ppm, J Hz, CDCl$_3$): 7.35–7.24(m,10H), 4.59(d,1H,J=12.3), 4.54(d,1H,J=12.3), 4.29–4.24(m,1H), 4.17(q,1H,J=6.7), 4.12–4.07(m,1H), 3.49(dd,1H,J=5.8,10.1), 3.37(dd,1H,J=4.6,10.1), 2.43(dd,1H,J=6.9,15.4), 2.30(dd,1H,J=5.8,15.4), 1.59(dt,$_1$H,J=2.5,12.8), 1.46(s,3H), 1.45(d,3H,J=6.8), 1.39(s,3H), 1.22(dt,1H,J=11.8,12.8).

To a mixed solution of 100 mg of the resulting (S)-1-phenylethylammonium (3R,5S)-6-benzyloxy-3,5-O-isopropylidene-3,5-dihydroxyhexanoate (10e) and toluene (2 ml), 0.24 ml of a 5% aqueous hydrochloric acid solution was added dropwise to make the amine free. A 2M hexane solution (0.12 ml) of trimethylsilyldiazomethane was added, whereby methyl (3R,5S)-6-benzyloxy-3,5-O-isopropylidene-3,5-dihydroxyhexanoate (1) was obtained. As a result of gas chromatography analysis, the syn-isomer/anti-isomer ratio was found to be 99.5/0.5.

GLC analysis
Column: Chirasil-Dex CB 0.25 mm×25 m (product of CHROMPACK)
Injection temperature: 200° C.
Column temperature: fixed at 170° C.
Detection temperature: 250° C.

Example 6

Synthesis of (R)-1-phenylethylammonium (3R,5S)-6-benzyloxy-3,5-O-isopropylidene-3,5-dihydroxyhexanoate (10f)

A 50 ml egg-plant type flask was charged with 781 mg (2.66 mmol) of the (3R,5S)-6-benzyloxy-3,5-O-isopropylidene-3,5-dihydroxyhexanoic acid (2) (syn-isomer/anti-isomer=95.3/4.7) obtained in Synthesis Example 1 and 5 ml of a mixed solvent (ethyl acetate/acetone/water=1/1/0.03). A solution of 420 mg (3.43 mmol) of (R)-1-phenylethylamine in 2 ml of a mixed solvent (ethyl acetate/acetone/water=1/1/0.03) was slowly added dropwise at 35° C. After completion of the dropwise addition, the reaction mixture was cooled to 5° C. Stirring was then conducted for 1 hour and the reaction mixture was filtered to isolate crystals. The resulting crystals were dried under reduced pressure, whereby 540 mg (1.30 mmol) of the target (R)-1-phenylethylammonium (3R,5S)-6-benzyloxy-3,5-O-isopropylidene-3,5-dihydroxyhexanoate (10f) was obtained as colorless crystals. The results are shown in Table 1.

Yield: 48.9%; Melting point: 69.7 to 70.3° C.; $^1$H-NMR (δ ppm, J Hz, CDCl$_3$): 7.35–7.23(m,10H) 4.59(d,1H,J=12.3), 4.53(d,1H,J=12.3), 4.28–4.23(m,1H), 4.17(q,1H,J=6.7), 4.11–4.06(m,1H), 3.48(dd,1H,J=5.8,10.0), 3.36(dd,1H, J=4.6,10.0), 2.40(dd,1H J=6.9,15.4), 2.27(dd,1H,J=5.8, 15.4), 1.60(dt,1E,J=2.3,12.8), 1.46(d,3H,J=6.6), 1.45(s,3H), 1.39(s,3H), 1.20(dt,1H,J=11.9,12.3).

To a mixed solution of 100 mg of the resulting (R)-1-phenylethylammonium (3R,5S)-6-benzyloxy- 3,5-O-isopropylidene-3,5-dihydroxyhexanoate (10f) and toluene (2 ml), 0.24 ml of a 5% aqueous hydrochloric acid solution was added dropwise to make the amine free. A 2M hexane solution (0.12 ml) of trimethylsilyldiazomethane was added, whereby methyl (3R,5S)-6-benzyloxy-3,5-O-isopropylidene-3,5-dihydroxyhexanoate (1) was obtained. As a result of gas chromatography analysis, the syn-isomer/anti-isomer ratio was found to be 99.7/0.3.

GLC analysis
Column: Chirasil-Dex CB 0.25 mm×25 m (product of CHROMPACK)
Injection temperature: 200° C.
Column temperature: fixed at 170° C.
Detection temperature: 250° C.

Example 7

Synthesis of (S)-2-hydroxy-1-phenylethylammonium (3R,5S)-6-benzyloxy-3,5-O-isopropylidene-3,5-dihydroxyhexanoate (10g)

A 50 ml egg-plant type flask was charged with 730 mg (2.48 mmol) of the (3R,5S)-6-benzyloxy-3,5-O-isopropylidene-3,5-dihydroxyhexanoic acid (2) (syn-isomer/anti-isomer=95.3/4.7) obtained in Synthesis Example 1 and 8 ml of ethyl acetate. A solution of 374 mg (2.73 mmol) of (S)-2-amino-2-phenylethanol in ethyl acetate (2 ml) was slowly added dropwise at 35° C. After completion of the dropwise addition, the reaction mixture was cooled to room temperature. Stirring was then conducted for 2 hours and then the reaction mixture was filtered to isolate crystals. The resulting crystals were dried under reduced pressure, whereby 720 mg (1.67 mmol) of the target (S)-2-hydroxy-1-phenylethylammonium (3R,5S)-6-benzyloxy-3,5-O-isopropylidene-3,5-dihydroxyhexanoate (10g) was obtained as colorless crystals. The results are shown in Table 1.

Yield: 67.4%; Melting point: 67.0 to 67.8° C.; $^1$H-NMR (δ ppm, J Hz, D$_2$O): 7.51–7.39(m,10H), 4.61(d,1H,J=12.0), 4.56(d,1H,J=11.9), 4.47(dd,1H,J=4.9,7.7), 4.41–4.39(m, 1H), 4.30–4.26(m,1H), 3.98(dd,1H,J=4.9,12.2), 3.92(dd,1H, J=7.7,12.2), 3.54(dd,1H,J=3.0,11.0), 3.48(dd,1H,J=7.1, 11.0), 2.40(dd,1H,J=6.9,14.4), 2.27(dd,1H,J=6.6,14.4), 1.59 (dt,1H,J=2.5,13.2), 1.53(s,3H), 1.40(s,3H), 1.22(dt,1H,J=11.8,13.2).

To a mixed solution of 100 mg of the resulting (S)-2-hydroxy-1-phenylethylammonium (3R,5S)-6-benzyloxy-3, 5-O-isopropylidene-3,5-dihydroxyhexanoate (10 g) and toluene (2 ml), 0.24 ml of a 5% aqueous hydrochloric acid solution was added dropwise to make the amine free. A 2M hexane solution (0.12 ml) of trimethylsilyldiazomethane was added, whereby methyl (3R,5S)-6-benzyloxy-3,5-O-isopropylidene-3,5-dihydroxyhexanoate (1) was obtained. As a result of gas chromatography analysis, the syn-isomer/anti-isomer ratio was found to be 100/0.

GLC analysis
Column: Chirasil-Dex CB 0.25 mm×25 m (product of CHROMPACK)
Injection temperature: 200° C.
Column temperature: fixed at 170° C.
Detection temperature: 250° C.

Example 8

Synthesis of (R)-2-hydroxy-1-phenylethylammonium (3R, 5S)-6-benzyloxy-3,5-O-isopropylidene-3,5-dihydroxyhexanoate (10h)

A 50 ml egg-plant type flask was charged with 793 mg (2.69 mmol) of the (3R,5S)-6-benzyloxy-3,5-O-isopropylidene-3,5-dihydroxyhexanoic acid (2) (syn-isomer/anti-isomer=95.3/4.7) obtained in Synthesis Example 1, 10 ml of methanol and 20 ml of ethyl acetate. A solution of 407 mg (2.97 mmol) of (R)-2-amino-2-phenylethanol in ethyl acetate (5 ml) was slowly added dropwise at 35° C. After completion of the dropwise addition, the reaction mixture was cooled to 10° C. Stirring was conducted for 1 hour and then the reaction mixture was filtered to isolate crystals. The resulting crystals were dried under reduced pressure, whereby the target (R)-2-hydroxy-1-phenylethylammonium (3R,5S)-6-benzyloxy-3,5-O-isopropylidene-3,5-dihydroxyhexanoate (10h) was obtained as colorless crystals. The results are shown in Table 1.

Yield: 62.1%; Melting point: 69.0 to 69.8° C.; $^1$H-NMR (δ ppm, J Hz, D$_2$O): 7.51–7.39(m,10H), 4.61(d,1H,J=12.0), 4.56(d,1H,J=11.9), 4.47(dd,1H,J=4.9,7.9), 4.41–4.39(m, 1H), 4.30–4.26(m,1H), 3.98(dd,1H,J=4.9,12.1), 3.92(dd,1H, J=7.9,12.1), 3.54(dd,1H,J=3.0,11.0), 3.48(dd,1H,J=7.1, 11.0), 2.40(dd,1H,J=6.9,14.4), 2.27(dd,1H,J=6.7,14.4), 1.59 (dt,1H,J=2.5,13.2), 1.53(s,3H), 1.40(s,3H), 1.22(dt,1H,J=11.8,13.1).

To a mixed solution of 100 mg of the resulting (R)-2-hydroxy-1-phenylethylammonium (3R,5S)-6-benzyloxy-3, 5-O-isopropylidene-3,5-dihydroxyhexanoate (10 h) and toluene (2 ml), 0.24 ml of a 5% aqueous hydrochloric acid solution was added dropwise to make the amine free. A 2M hexane solution (0.12 ml) of trimethylsilyldiazomethane was added, whereby methyl (3R,5S)-6-benzyloxy-3,5-O-isopropylidene-3,5-dihydroxyhexanoate (1) was obtained. As a result of gas chromatography analysis, the syn-isomer/anti-isomer ratio was found to be 99.7/0.3.

GLC analysis

Column: Chirasil-Dex CB 0.25 mm×25 m (product of CHROMPACK)

Injection temperature: 200° C.

Column temperature: fixed at 170° C.

Detection temperature: 250° C.

Example 9

Synthesis of dicyclohexylammonium (3R,5S)-6-benzyloxy-3,5-O-isopropylidene-3,5-dihydroxyhexanoate (10 i)

A 50 ml egg-plant type flask was charged with 778 mg (2.64 mmol) of the (3R,5S)-6-benzyloxy-3,5-O-isopropylidene-3,5-dihydroxyhexanoic acid (2) (syn-isomer/anti-isomer=95.3/4.7) obtained in Synthesis Example 1 and 15 ml of ethyl acetate. A solution of 480 mg (2.65 mmol) of dicyclohexylamine in ethyl acetate (2 ml) was slowly added dropwise at 35° C. After completion of the dropwise addition, the reaction mixture was cooled to room temperature. Stirring was then conducted for 30 minutes and then the reaction mixture was filtered to isolate crystals. The resulting crystals were dried under reduced pressure, whereby 599 mg (1.26 mmol) of the target dicyclohexylammonium (3R,5S)-6-benzyloxy-3,5-O-isopropylidene-3,5-dihydroxyhexanoate (10i) was obtained as colorless crystals. The results are shown in Table 1.

Yield: 47.8%; Melting point: 71.0 to 71.7° C.; $^1$H-NMR (δ ppm, J Hz, CDCl$_3$): 7.33–7.26(m,5H), 4.60(d,1H,J=12.3), 4.53(d,1H,J=12.3), 4.35–4.32(m,1H), 4.13–4.11(m,1H), 3.48(dd,1H,J=6.0,10.0), 3.36(dd,$_1$H,J=4.4,10.0), 2.88–2.83 (m,1H), 2.46(dd,1H,J=6.3,14.8), 2.26(dd,1H,J=7.1,14.8), 1.98(d,4H,J=12.3), 1.76(d,4H,J=12.8), 1.69(dt,1H,J=2.4, 12.8), 1.62(d,2H,J=11.6), 1.48(s,3H), 1.39–1.32(m,7H), 1.26–1.13(m,7H).

To a mixed solution of 100 mg of the resulting dicyclohexylammonium (3R,5S)-6-benzyloxy-3,5-O-isopropylidene-3,5-dihydroxyhexanoate (10 i) and toluene (2 ml), 0.21 ml of a 5% aqueous hydrochloric acid solution was added dropwise to make the amine free. A 2M hexane solution (0.11 ml) of trimethylsilyldiazomethane was added, whereby methyl (3R,5S)-6-benzyloxy-3,5-O-isopropylidene-3,5-dihydroxyhexanoate (1) was obtained. As a result of gas chromatography analysis, the syn-isomer/anti-isomer was found to be 99.7/0.3.

GLC analysis

Column: Chirasil-Dex CB 0.25 mm×25 m (product of CHROMPACK)

Injection temperature: 200° C.

Column temperature: fixed at 170° C.

Detection temperature: 250° C.

Example 10

Synthesis of cinchoninium (3R,5S)-6-benzyloxy-3,5-O-isopropylidene-3,5-dihydroxyhexanoate (10j)

A 50 ml egg-plant type flask was charged with 780 mg (2.65 mmol) of the (3R,5S)-6-benzyloxy-3,5-O-isopropylidene-3,5-dihydroxyhexanoic acid (2) (syn-isomer/anti-isomer=95.3/4.7) obtained in Synthesis Example 1 and 7 ml of a mixed solvent (ethyl acetate/acetone/water=1/1/0.03)). Cinchonine (694 mg, 2.79 mmol) was then added dropwise at 35° C. After completion of the addition, the reaction mixture was cooled to room temperature. Stirring was conducted for 2 hours and then the reaction mixture was filtered to isolate crystals. The resulting crystals were dried under reduced pressure, whereby 278 mg (0.52 mmol) of the target cinchoninum (3R,5S)-6-benzyloxy-3,5-O-isopropylidene-3,5-dihydroxyhexanoate (10j) was obtained as colorless crystals. The results are shown in Table 1.

Yield: 19.3%; Melting point: 179.4 to 180.0° C.; To a mixed solution of 100 mg of the resulting cinchoninum (3R,5S)-6-benzyloxy-3,5-O-isopropylidene-3,5-dihydroxyhexanoate (10 i) and toluene (2 ml), 0.18 ml of a 5% aqueous hydrochloric acid solution was added dropwise to make the amine free. A 2M hexane solution (0.09 ml) of trimethylsilyldiazomethane was added, whereby methyl (3R,5S)-6-benzyloxy-3,5-O-isopropylidene-3,5-dihydroxyhexanoate (1) was obtained. As a result of gas chromatography analysis, the syn-isomer/anti-isomer ratio was found to be 95.3/4.7.

GLC analysis

Column: Chirasil-Dex CB 0.25 mm×25 m (product of CHROMPACK)

Injection temperature: 200° C.

Column temperature: fixed at 170° C.

Detection temperature: 250° C.

Example 11

Synthesis of cinchonidinium (3R,5S)-6-benzyloxy-3,5-O-isopropylidene-3,5-dihydroxyhexanoate (10k)

A 50 ml egg-plant type flask was charged with 810 mg (2.75 mmol) of the (3R,5S)-6-benzyloxy-3,5-O-isopropylidene-3,5-dihydroxyhexanoic acid (2) (syn-isomer/anti-isomer=95.3/4.7) obtained in Synthesis Example 1, 1 ml of ethyl acetate and 5 ml of hexane. Cinchonidine (720 mg, 2.89 mmol) was then added dropwise at 35° C. After completion of the dropwise addition, the reaction mixture was cooled to room temperature. Stirring was conducted for 2 hours and then the reaction mixture was filtered to isolate crystals. The resulting crystals were dried under reduced pressure, whereby 223 mg (0.41 mmol) of the target cinchonidinium (3R,5S)-6-benzyloxy-3,5-O-isopropylidene-3,5-dihydroxyhexanoate (10k) was obtained as colorless crystals. The results are shown in Table 1.

Yield: 14.9%; Melting point: 139.2 to 140.6° C.; $^1$H-NMR (δ ppm, J Hz, CDCl$_3$): 8.88(d,2H,J=4.4), 8.08(d,2H,J=8.2), 7.89(d,2H,J=8.2), 7.65–7.61(m,4H), 7.40–7.37(m,2H), 7.34–7.26(m,5H), 5.91(br,2H), 5.68–5.60(m,2H), 4.97(dd, 2H,J=1.2,17.2), 4.92(dd,2H,J=1.0,10.3), 4.55(d,1H,J=12.3), 4.48(d,1H,J=12.3), 4.36–4.29(m,1H), 4.11–4.02(m,1H), 3.81(br,2H), 3.40(dd,1H,J=6.0,10.1), 3.25(dd,1H,J=4.4, 10.1), 3.23–3.14(m,4H), 2.87–2.75(m,4H), 2.54(dd,1H,J= 5.8,14.8), 2.39(br,2H), 2.31(dd,1H,J=7.5,14.8), 1.89–1.80 (m,6H), 1.67(dt,1H,J=2.3,12.8), 1.58(br,2H), 1.40–1.36(m, 5H), 1.32(s,3H), 1.20–1.11(m,1H).

To a mixed solution of 100 mg of the resulting cinchonidinium (3R,5S)-6-benzyloxy-3,5-O-isopropylidene-3, 5-dihydroxyhexanoate (10k) and toluene (2 ml), 0.18 ml of a 5% aqueous hydrochloric acid solution was added dropwise to make the amine free. A 2M hexane solution (0.09 ml) of trimethylsilyldiazomethane was added, whereby methyl (3R,5S)-6-benzyloxy- 3,5-O-isopropylidene-3,5-dihydroxyhexanoate (1) was obtained. As a result of gas chromatography analysis, the syn-isomer/anti-isomer ratio was found to be 99.0/1.0.

GLC analysis

Column: Chirasil-Dex CB 0.25 mm×25 m (product of CHROMPACK)

Injection temperature: 200° C.
Column temperature: fixed at 170° C.
Detection temperature: 250° C.

Comparative Example 1

A 50 ml egg-plant type flask was charged with 750 mg (2.55 mmol) of the (3R,5S)-6-benzyloxy-3,5-O-isopropylidene-3,5-dihydroxyhexanoic acid (2) (syn-isomer/anti-isomer=95.3/4.7) obtained in Synthesis Example 1 and 3.0 ml of ethyl acetate. A solution of 261 mg (2.81 mmol) of aniline in ethyl acetate (2 ml) was then slowly added dropwise at 35° C. After completion of the dropwise addition, the reaction mixture was cooled to 20° C. Stirring was conducted for 1 hour, but no crystals were precipitated. The solvent was therefore distilled off from the reaction mixture, but the residue was obtained in not solidified but liquid form. The liquid residue thus obtained was frozen at −30° C. and stored for 12 hours, but no solidification occurred. The results are shown in Table 1.

Comparative Examples 2 to 10

In each of Comparative Examples 2 to 10, operation was conducted under similar conditions to Comparative Example 1 by using the amine (m to u) as shown in Table 1. No solidification, however, occurred. The results are shown in Table 1.

TABLE 1

| | Compound | Amine (A) | Yield | Syn/Anti |
|---|---|---|---|---|
| Ex. 1 | 10a | $(C_6H_{11})NH_2$ | 87.8 | 99.8/0.2 |
| Ex. 2 | 10b | $(CH_3)_3CNH_2$ | 80.8 | 99.4/0.6 |
| Ex. 3 | 10c | $CH_3(CH_2)_2NH_2$ | 62.0 | 99.1/0.9 |
| Ex. 4 | 10d | $C_6H_5CH_2NH_2$ | 64.3 | 99.0/1.0 |
| Ex. 5 | 10e | $(S)-C_6H_5CH(CH_3)NH_2$ | 92.1 | 99.5/0.5 |
| Ex. 6 | 10f | $(R)-C_6H_5CH(CH_3)NH_2$ | 48.9 | 99.7/0.3 |
| Ex. 7 | 10g | $(S)-C_6H_5CH(NH_2)CH_2OH$ | 67.4 | 100/0.0 |
| Ex. 8 | 10h | $(R)-C_6H_5CH(NH_2)CH_2OH$ | 62.1 | 99.7/0.3 |
| Ex. 9 | 10i | $(C_6H_{11})_2NH$ | 47.8 | 99.7/0.3 |
| Ex. 10 | 10j | Cinchonine | 19.3 | 95.3/4.7 |
| Ex. 11 | 10k | Cinchonidine | 14.9 | 99.0/1.0 |
| Comp. Ex. 1 | 10l | $C_6H_5NH_2$ | — | — |
| Comp. Ex. 2 | 10m | (S)-2-Pyrrolidinemethanol | — | — |
| Comp. Ex. 3 | 10n | (R)-2-Pyrrolidinemethanol | — | — |
| Comp. Ex. 4 | 10o | $[(CH_3)_2CH]_2NH$ | — | — |
| Comp. Ex. 5 | 10p | $(C_2H_5)_2NH$ | — | — |
| Comp. Ex. 6 | 10q | $(C_6H_5CH_2)_2NH$ | — | — |
| Comp. Ex. 7 | 10r | $(C_2H_5)_3N$ | — | — |
| Comp. Ex. 8 | 10s | 4-Dimethylaminopyridine | — | — |
| Comp. Ex. 9 | 10t | $H_2NCH_2CH_2NH_2$ | — | — |
| Comp. Ex. 10 | 10u | $NH_3$ | — | — |

As is apparent from Table 1, when the reaction was conducted using an alkyl or aralkyl-containing primary amine (Examples 2 to 8), an alicyclic primary amine (Example 1) or an alicyclic secondary amine (Example 9), the target ammonium (3R,5S)-3,5,6-trihydroxyhexanoate composed of the syn-isomer at a high purity, more specifically, 99.0% or greater was obtained in a high yield.

When the reaction was conducted using cinchonine or cinchonidine (Example 10 or 11), the yield did not reach 20%. When an aryl-containing primary amine (Comparative Example 1), a secondary amine other than alicyclic secondary amine (Comparative Examples 2 to 6), a tertiary amine (Comparative Example 7 and 8), diamine (Comparative Example 9) or ammonia (Comparative Example 10) was used, no solidification occurred even after storage under frozen state at −30° C. for 12 hours, meaning that the ammonium (3R,5S)-6-benzyloxy-3,5-O-isopropylidene-3,5-dihydroxyhexanoate (10l to 10u) had a melting point of −30° C. or less and was not handled as crystals.

In Synthesis Example 1(2), as a result of hydrolysis of methyl (3R,5S)-6-benzyloxy-3,5-O-isopropylidene-3,5-dihydroxyhexanoate using sodium hydroxide, sodium (3R,5S)-6-benzyloxy-3,5-O-isopropylidene-3,5-dihydroxyhexanoate was formed in the reaction system. As is apparent from Synthesis Example 1(2), it was soluble in water because of markedly high aqueous solubility, which made it utterly difficult to obtain the product as crystals.

As described above, use of an alkyl or aralkyl-containing primary amine, alicyclic primary amine or alicyclic primary amine is useful for completion of the present reaction in the invention.

Example 12

Synthesis of cyclohexylammonium (3R,5S)-6-triphenylmethoxy-3,5-O-isopropylidene-3,5-dihydroxyhexanoate (11a)

A 50 ml egg-plant type flask was charged with 750 mg (1.68 mmol) of the (3R,5S)-6-triphenylmethoxy-3,5-O-isopropylidene-3,5-dihydroxyhexanoic acid (5a) (syn-isomer/anti-isomer=98.0/2.0) obtained in Synthesis Example 2 and 8.0 ml of diisopropyl ether. A solution of 200 mg (2.02 mmol) of cyclohexylamine in diisopropyl ether (2.0 ml) was slowly added dropwise at room temperature. After completion of the dropwise addition, stirring was conducted for 30 minutes. The reaction mixture was then filtered to isolate crystals. The resulting crystals were dried under reduced pressure, whereby 770 mg (1.41 mmol) of the target cyclohexylammonium (3R,5S)-6-triphenylmethoxy-3,5-O-isopropylidene-3,5-dihydroxyhexanoate (11a) was obtained as colorless crystals. The results are shown in Table 2.

Yield: 83.9%; Melting point: 71.9 to 72.2° C.; $^1$H-NMR (δ ppm, J Hz, CDCl$_3$): 7.45(d,6H,J=8.1), 7.29–7.19(m,9H), 4.31–4.28(m,1H), 4.07–4.04(m,1H), 3.21(dd,1H,J=5.6,9.3), 2.93(dd,1H,J=5.4,9.3), 2.90–2.80(m,1H), 2.35(dd,1H,J=6.8, 15.0), 2.24(dd,1H,J=5.8,15.0), 1.94–1.91(m,2H), 1.71–1.66 (m,3H), 1.59–1.52(m,1H), 1.45(s,3H), 1.37(s,3H), 1.30–1.05(m,6H).

To a mixed solution of 100 mg of the resulting cyclohexylammonium (3R,5S)-6-triphenylmethoxy-3,5-O-isopropylidene-3,5-dihydroxyhexanoate (11a) and toluene (2 ml), 0.18 ml of a 5% aqueous hydrochloric acid solution was added dropwise to make the amine free. A 2M hexane solution (0.09 ml) of trimethylsilyldiazomethane was added, whereby methyl (3R,5S)-6-triphenylmethoxy-3,5-O-isopropylidene-3,5-dihydroxyhexanoate (4a) was obtained. As a result of an analysis by high-performance liquid chromatography, the syn-isomer/anti-isomer ratio was found to be 99.8/0.2.

Example 13

Synthesis of tert-butylammonium (3R,5S)-triphenylmethoxy-3,5-O-isopropylidene-3,5-dihydroxyhexanoate (11b)

A 50 ml egg-plant type flask was charged with 472 mg (1.06 mmol) of the (3R,5S)-6-triphenylmethoxy-3,5-O-isopropylidene-3,5-dihydroxyhexanoic acid (5a) (syn-isomer/anti-isomer=98.0/2.0) obtained in Synthesis Example 2 and 5.0 ml of diisopropyl ether. A solution of 85 mg (1.16 mmol) of tert-butylamine in diisopropyl ether (0.5 ml) was slowly added dropwise at room temperature. After completion of the dropwise addition, stirring was conducted for 30 minutes. The reaction mixture was then filtered to isolate crystals. The resulting crystals were dried under reduced pressure, whereby 280 mg (0.541 mmol) of the target tert-butylammonium (3R,5S)-6-triphenylmethoxy-3,5-O-isopropylidene-3,5-dihydroxyhexanoate (11b) was obtained as colorless crystals. The results are shown in Table 2.

Yield: 51.0%; Melting point: 70.6 to 71.4° C.; $^1$H-NMR (δ ppm, J Hz, CDCl$_3$): 7.45(d,6H,J=8.1), 7.28–7.19(m,9H), 4.36–4.31(m,1H), 4.05–4.02(m,1H), 3.21(dd,1H,J=5.4,9.2), 2.94(dd,1H,J=5.8,9.2), 2.37(dd,1H,J=7.2,15.0), 2.26(dd,1H, J=5.6,15.0), 1.73(dt,1H,J=2.4,12.8), 1.43(s,3H), 1.34(s,3H), 1.28(s,9H), 1.18(dt,1H,J=11.8,12.8).

To a mixed solution of 100 mg of the resulting tert-butylammonium (3R,5S)-triphenylmethoxy-3,5-O-isopropylidene-3,5-dihydroxyhexanoate (11b) and toluene (2 ml), 0.19 ml of a 5% aqueous hydrochloric acid solution was added dropwise to make the amine free. A 2M hexane solution (0.10 ml) of trimethylsilyldiazomethane was added, whereby methyl (3R,5S)-6-triphenylmethoxy-3,5-O-isopropylidene-3,5-dihydroxyhexanoate (4a) was obtained. As a result of an analysis by high-performance liquid chromatography, the syn-isomer/anti-isomer ratio was found to be 99.6/0.4.

HPLC analysis

Column: Inertsil ODS-2 4.6×250 mm (product of GL Science)

Eluent: acetonitrile/water (150 ppm phosphoric acid)=7/3

Flow rate: 0.5 ml/min

Detection: UW 220 nm

Example 14

Synthesis of (S)-1-phenylethylammonium (3R,5S)-6-triphenylmethoxy-3,5-O-isopropylidene-3,5-dihydroxyhexanoate (11c)

A 50 ml egg-plant type flask was charged with 450 mg (1.01 mmol) of the (3R,5S)-6-triphenylmethoxy-3,5-O-isopropylidene-3,5-dihydroxyhexanoic acid (2) (syn-isomer/anti-isomer=98.0/2.0) obtained in Synthesis Example 2 and 5.0 ml of diisopropyl ether. A solution of 133 mg (1.10 mmol) of (S)-1-phenylethylamine in diisopropyl ether (0.5 ml) was slowly added dropwise at room temperature. After completion of the dropwise addition, stirring was conducted at −20° C. for 30 minutes. The reaction mixture was filtered to isolate crystals. The resulting crystals were dried under reduced pressure, whereby 460 mg (0.810 mmol) of the target (S)-1-phenylethylammonium (3R,5S)-6-triphenylmethoxy-3,5-O-isopropylidene-3,5-dihydroxyhexanoate (11c) was obtained as colorless crystals. The results are shown in Table 2.

Yield: 80.2%; Melting point: 68.2 to 69.0° C.; $^1$H-NMR (δ ppm, J Hz, CDCl$_3$): 7.45(d,6H,J=8.2), 7.33–7.20(m,14H), 4.28–4.22(m,1H), 4.17(q,1H,J=6.7), 4.09–3.98(m,1H), 3.22 (dd,1H,J=5.5,9.3), 2.95(dd,1H,J=5.6,9.3), 2.37(dd,1H,J=7.1,15.5), 2.26(dd,1H,J=5.5,15.5), 1.63(dt,1H,J=2.4,12.8), 1.46(d,3H,J=6.7), 1.44(s,3H), 1.36(s,3H), 1.17(dt,1H,J=11.7,12.8).

To a mixed solution of 100 mg of the resulting (S)-1-phenylethylammonium (3R,5S)-6-triphenylmethoxy-3,5-O-isopropylidene-3,5-dihydroxyhexanoate (11c) and toluene (2 ml), 0.18 ml of a 5% aqueous hydrochloric acid solution was added dropwise to make the amine free. A 2M hexane solution (0.09 ml) of trimethylsilyldiazomethane was added, whereby methyl (3R,5S)-6-triphenylmethoxy-3,5-O-isopropylidene-3,5-dihydroxyhexanoate (4a) was obtained. As a result of an analysis by high-performance liquid chromatography, the syn-isomer/anti-isomer ratio was found to be 100/0.

HPLC analysis

Column: Inertsil ODS-2 4.6×250 mm (product of GL Science)

Eluent: acetonitrile/water (150 ppm phosphoric acid)=7/3

Flow rate: 0.5 ml/min

Detection: UV 220 nm

Example 15

Synthesis of cyclohexylammonium (3R,5S)-6-tert-butyldimethylsilyloxy-3,5-O-isopropylidene-3,5-dihydroxyhexanoate (11d)

A 50 ml egg-plant type flask was charged with 1000 mg (3.14 mmol) of the (3R,5S)-6-tert-butyldimethylsilyloxy-3,5-O-isopropylidene-3,5-dihydroxyhexanoic acid (5b) (syn-isomer/anti-isomer=98.5/1.5) obtained in Synthesis Example 3 and 8.5 ml of a mixed solvent (ethyl acetate/acetone/water=1/1/0.03). A solution of 343 mg (3.46 mmol) of cyclohexylamine in 0.5 ml of a mixed solvent (ethyl acetate/acetone/water=1/1/0.03) was slowly added dropwise at room temperature. After completion of the dropwise addition, stirring was conducted for 2 hours. The reaction mixture was then filtered to isolate crystals. The resulting crystals were dried under reduced pressure, whereby 1085 mg (2.60 mmol) of the target cyclohexylammonium (3R,5S)-6-tert-butyldimethylsilyloxy-3,5-O-isopropylidene-3,5-dihydroxyhexanoate (11d) was obtained as colorless crystals. The results are shown in Table 2.

Yield: 82.7%; Melting point: 65.9 to 66.8° C.; $^1$H-NMR (δ ppm, J Hz, CDCl$_3$): 4.35–4.25(m,1H), 3.96–3.88(m,1H), 3.63(dd,1H,J=5.4,10.4), 3.48(dd,1H,J=5.5,10.4), 2.90–2.86 (m,1H), 2.36(dd,1H,J=6.7,14.9), 2.24(dd,1H,J=6.0,14.9), 1.98(d,2H,J=11.0), 1.77(d,2H,J=12.5), 1.69–1.62(m,2H), 1.44(s,3H), 1.35(s,3H), 1.33–1.22(m,4H), 1.20–1.09(m,2H), 0.89(s,9H), 0.05(s,6H)

To a mixed solution of 100 mg of the resulting cyclohexylammonium (3R,5S)-6-tert-butyldimethylsilyloxy-3,5-O-isopropylidene-3,5-dihydroxyhexanoate (11d) and toluene (2 ml), 0.25 ml of a 5% aqueous hydrochloric acid solution was added dropwise to make the amine free. A 2M hexane solution (0.13 ml) of trimethylsilyldiazomethane was added, whereby methyl (3R,5S)-6-tert-butyldimethyloxy-3,5-O-isopropylidene-3,5-dihydroxyhexanoate (4b) was obtained. As a result of an analysis by high-performance liquid chromatography, the syn-isomer/anti-isomer ratio was found to be 99.4/0.6.

GLC analysis
Column: TC-5HT 0.25 mm×30 m (product of GL Science)
Injection temperature: 200° C.
Column temperature: 150° C.-(5° C./min)–200° C.-(10° C./min)–250° C. (kept for 15 min)
Detection temperature: 250° C.

Example 16
Synthesis of tert-butylammonium (3R,5S)-6-tert-butyldimethylsilyloxy-3,5-O-isopropylidene-3,5-dihydroxyhexanoate (11e)

A 50 ml egg-plant type flask was charged with 1000 mg (3.14 mmol) of the (3R,5S)-6-tert-butyldimethylsilyloxy-3,5-O-isopropylidene-3,5-dihydroxyhexanoic acid (5b) (syn-isomer/anti-isomer=98.5/1.5) obtained in Synthesis Example 3 and 8.5 ml of a mixed solvent (ethyl acetate/acetone/water=1/1/0.03). A solution of 253 mg (3.46 mmol) of tert-butylamine in 0.5 ml of a mixed solvent (ethyl acetate/acetone/water=1/1/0.03) was slowly added dropwise at room temperature. After completion of the dropwise addition, stirring was conducted for 2 hours. The reaction mixture was then filtered to isolate crystals. The resulting crystals were dried under reduced pressure, whereby 956 mg (2.44 mmol) of the target tert-butylammonium (3R,5S)-6-tert-butyldimethylsilyloxy-3,5-O-isopropylidene-3,5-dihydroxyhexanoate (11e) was obtained as colorless crystals. The results are shown in Table 2.

Yield: 77.7%; Melting point: 55.2 to 56.0° C.; $^1$H-NMR ($\delta$ ppm, J Hz, CDCl$_3$): 4.36–4.30(m,1H), 3.95–3.90(m,1H), 3.64(dd,1H,J=5.3,10.3), 3.46(dd,1H,J=5.9,10.3), 2.38(dd,1H,J=6.8,14.9), 2.24(dd,1H,J=6.1,14.9), 1.73(dt,1H,J=2.4,12.7), 1.43(s,3H), 1.33(s,3H), 1.31(s,9H), 1.12(dt,1H,J=11.7,12.5), 0.87(s,9H), 0.04(s,6H).

To a mixed solution of 100 mg of the resulting tert-butylammonium (3R,5S)-6-tert-butyldimethylsilyloxy-3,5-O-isopropylidene-3,5-dihydroxyhexanoate (11e) and toluene (2 ml), 0.27 ml of a 5% aqueous hydrochloric acid solution was added dropwise to make the amine free. A 2M hexane solution (0.14 ml) of trimethylsilyldiazomethane was added, whereby methyl (3R,5S)-6-tert-butyldimethyloxy-3,5-O-isopropylidene-3,5-dihydroxyhexanoate (4b) was obtained. As a result of gas chromatography analysis, the syn-isomer/anti-isomer ratio was found to be 99.8/0.2.

GLC analysis
Column: TC-5HT 0.25 mm×30 m (product of GL Science)
Injection temperature: 200° C.
Column temperature: 150° C.-(5° C./min)–200° C.-(10° C./min)–250° C. (kept for 15 min)
Detection temperature: 250° C.

Example 17
Synthesis of (S)-1-phenylethylammonium (3R,5S)-6-tert-butyldimethylsilyloxy-3,5-O-isopropylidene-3,5-dihydroxyhexanoate (11f)

A 50 ml egg-plant type flask was charged with 925 mg (2.90 mmol) of the (3R,5S)-6-tert-butyldimethylsilyloxy-3,5-O-isopropylidene-3,5-dihydroxyhexanoic acid (5b) (syn-isomer/anti-isomer=98.5/1.5) obtained in Synthesis Example 3 and 8.5 ml of a mixed solvent (ethyl acetate/acetone/water=1/1/0.03). A solution of 387 mg (3.19 mmol) of (S)-1-phenylethylamine in 0.5 ml of a mixed solvent (ethyl acetate/acetone/water=1/1/0.03) was slowly added dropwise at room temperature. After completion of the dropwise addition, stirring was conducted for 2 hours. The reaction mixture was then filtered to isolate crystals. The resulting crystals were dried under reduced pressure, whereby 976 mg (2.22 mmol) of the target (S)-1-phenylethylammonium (3R,5S)-6-tert-butyldimethylsilyloxy-3,5-O-isopropylidene-3,5-dihydroxyhexanoate (11f) was obtained as colorless crystals. The results are shown in Table 2.

Yield: 76.5%; Melting point: 71.0 to 71.8° C.; $^1$H-NMR ($\delta$ ppm, J Hz, CDCl$_3$): 7.38–7.26(m,5H), 4.22–4.13(m,2H), 3.87–3.84(m,1H), 3.62(dd,1H,J=5.3,10.3), 3.46(dd,1H,J=5.6,10.3), 2.21–2.16(m,1H), 2.04–1.99(m,1H), 1.56–1.53(m,1H), 1.50(d,3H,J=6.8), 1.40(s,3H), 1.32(s,3H), 1.08–1.01(m,1H), 0.89(s,9H), 0.05(s,6H).

To a mixed solution of 100 mg of the resulting (S)-1-phenylethylammonium (3R,5S)-6-tert-butyldimethylsilyloxy-3,5-O-isopropylidene-3,5-dihydroxyhexanoate (11f) and toluene (2 ml), 0.24 ml of a 5% aqueous hydrochloric acid solution was added dropwise to make the amine free. A 2M hexane solution (0.12 ml) of trimethylsilyldiazomethane was added, whereby methyl (3R,5S)-6-tert-butyldimethyloxy-3,5-O-isopropylidene-3,5-dihydroxyhexanoate (4b) was obtained. As a result of an analysis by gas chromatography analysis, the syn-isomer/anti-isomer ratio was found to be 99.8/0.2.

GLC analysis
Column: TC-5HT 0.25 mm×30 m (product of GL Science)
Injection temperature: 200° C.
Column temperature: 150° C.-(5° C./min)–200° C.-(10° C./min)–250° C. (kept for 15 min)
Detection temperature: 250° C.

Example 18
Synthesis of cyclohexylammonium (3R,5S)-6-acetoxy-3,5-O-isopropylidene-3,5-dihydroxyhexanoate (11g)

A 50 ml egg-plant type flask was charged with 500 mg (2.03 mmol) of the (3R,5S)-6-acetoxy-3,5-O-isopropylidene-3,5-dihydroxyhexanoic acid (9) (syn-isomer/anti-isomer=97.8/2.2) obtained in Synthesis Example 4 and 2.0 ml of ethyl acetate. A solution of 221 mg (2.23 mmol) of cyclohexylamine in ethyl acetate (0.5 ml) was slowly added dropwise at room temperature. After completion of the dropwise addition, stirring was conducted for 30 minutes. The reaction mixture was then filtered to separate crystals. The resulting crystals were dried under reduced pressure, whereby 596 mg (1.73 mmol) of the target cyclohexylammonium (3R,5S)-6-acetoxy-3,5-O-isopropylidene-3,5-dihydroxyhexanoate (11g) was obtained as colorless crystals. The results are shown in Table 2.

Yield: 85.2%; Melting point: 67.9 to 68.8° C.; $^1$H-NMR ($\delta$ ppm, J Hz, CDCl$_3$): 4.26–4.21(m,1H), 4.07–4.02(m,1H), 3.99(dd,1H,J=3.8,11.5), 3.93(dd,1H,J=6.3,11.5), 2.87–2.77(m,1H), 2.33(dd,$_1$H,J=6.5,15.0), 2.18(dd,1H,J=6.5,15.0), 2.01(s,3H), 1.95–1.86(m,2H), 1.73–1.67(m,2H), 1.62–1.52(m,2H), 1.39(s,3H), 1.32(s,3H), 1.30–1.03(m,6H).

To a mixed solution of 100 mg of the resulting cyclohexylainmonium (3R,5S)-6-acetoxy-3,5-O-isopropylidene-3,5-dihydroxyhexanoate (11g) and toluene (2 ml), 0.29 ml of a 5% aqueous hydrochloric acid solution was added dropwise to make the amine free. A 2M hexane solution (0.15 ml) of trimethylsilyldiazomethane was added, whereby methyl (3R,5S)-6-acetoxy-3,5-O-isopropylidene-3,5-dihydroxyhexanoate was obtained. As a result of gas chromatography analysis, the syn-isomer/anti-isomer ratio was found to be 99.8/0.2.

GLC analysis
- Column: Chirasil-Dex CB 0.25 mm×25 m (product of CHROMPACK)
- Injection temperature: 200° C.
- Column temperature: fixed at 150° C.
- Detection temperature: 250° C.

Example 19
Synthesis of tert-butylammonium (3R,5S)-6-acetoxy-3,5-O-isopropylidene-3,5-dihydroxyhexanoate (11h)

A 50 ml egg-plant type flask was charged with 526 mg (2.14 mmol) of the (3R,5S)-6-acetoxy-3,5-O-isopropylidene-3,5-dihydroxyhexanoic acid (9) (syn-isomer/anti-isomer=97.8/2.2) obtained in Synthesis Example 4 and 4.0 ml of a mixed solvent (ethyl acetate/acetone/water=1/1/0.03). A solution of 171 mg (2.23 mmol) of tert-butylamine in 0.5 ml of a mixed solvent (ethyl acetate/acetone/water=1/1/0.03) was slowly added dropwise at 40° C. After completion of the dropwise addition, the temperature of the reaction mixture was allowed to rise back to room temperature over 1 hour. The reaction mixture was then filtered to isolate crystals. The resulting crystals were dried under reduced pressure, whereby 606 mg (1.90 mmol) of the target tert-butylammonium (3R,5S)-6-acetoxy-3,5-O-isopropylidene-3,5-dihydroxyhexanoate (11h) was obtained as colorless crystals. The results are shown in Table 2.

Yield: 88.8%; Melting point: 63.2 to 64.0° C.; $^1$H-NMR (δ ppm, J Hz, D$_2$O): 4.48–4.33(m,2H), 4.17(dd,1H,J=2.7, 12.0), 4.01(dd,1H,J=6.7,12.0), 2.42(dd,1H,J=7.0,14.4), 2.31 (dd,1H,J=6.5,14.4), 2.11(s,3H), 1.67(dt,1H,J=2.3,13.2), 1.55(s,3H), 1.40(s,3H), 1.39–1.27(m,10H).

To a mixed solution of 100 mg of the resulting tert-butylammonium (3R,5S)-6-acetoxy-3,5-O-isopropylidene-3,5-dihydroxyhexanoate (11h) and toluene (2 ml), 0.31 ml of a 5% aqueous hydrochloric acid solution was added dropwise to make the amine free. A 2M hexane solution (0.16 ml) of trimethylsilyldiazomethane was added, whereby methyl (3R,5S)-6-acetoxy-3,5-O-isopropylidene-3,5-dihydroxyhexanoate was obtained. As a result of gas chromatography analysis, the syn-isomer/anti-isomer ratio was found to be 99.8/0.2.

GLC analysis
- Column: Chirasil-Dex CB 0.25 mm×25 m (product of CHROMPACK)
- Injection temperature: 200° C.
- Column temperature: fixed at 150° C.
- Detection temperature: 250° C.

Example 20
Synthesis of (S)-1-phenylethylammonium (3R,5S)-6-acetoxy-3,5-O-isopropylidene-3,5-dihydroxyhexanoate (11i)

A 50 ml egg-plant type flask was charged with 526 mg (2.14 mmol) of the (3R,5S)-6-acetoxy-3,5-O-isopropylidene-3,5-dihydroxyhexanoic acid (9) (syn-isomer/anti-isomer=97.8/2.2) obtained in Synthesis Example 4 and 6.0 ml of a mixed solvent (ethyl acetate/acetone/water=1/1/0.03). A solution of 286 mg (2.36 mmol) of (S)-1-phenylethylamine in 0.5 ml of a mixed solvent (ethyl acetate/acetone/water=1/1/0.03) was slowly added dropwise at 40° C. After completion of the dropwise addition, the reaction mixture was allowed to cool down to room temperature over 2 hours. Filtration was conducted to isolate crystals. The resulting crystals were dried under reduced pressure, whereby the target (S)-1-phenylethylammonium (3R-,5S)-6-acetoxy-3,5-O-isopropylidene-3,5-dihydroxyhexanoate (11i) was obtained as colorless crystals. The results are shown in Table 2.

Yield: 86.9%; Melting point: 68.0 to 69.2° C.; $^1$H-NMR (δ ppm, J Hz, CDCl$_3$): 7.30–7.20(m,5H), 4.20–4.17(m,1H), 4.12(q,1H,J=6.7), 4.06–3.90(m,3H), 2.32(dd,1H,J=6.8, 15.4), 2.17(dd,1H,J=6.1,15.4), 2.02(s,3H), 1.50–1.44(m, 1H), 1.42(d,3H,J=6.7), 1.38(s,3H), 1.31(s,3H), 1.13(dt,1H, J=11.7,12.4).

To a mixed solution of 100 mg of the resulting (S)-1-phenylethylammonium (3R,5S)-6-acetoxy-3,5-O-isopropylidene-3,5-dihydroxyhexanoate (11i) and toluene (2 ml), 0.27 ml of a 5% aqueous hydrochloric acid solution was added dropwise to make the amine free. A 2M hexane solution (0.14 ml) of trimethylsilyldiazomethane was added, whereby methyl (3R,5S)-6-acetoxy-3,5-O-isopropylidene-3,5-dihydroxyhexanoate was obtained. As a result of gas chromatography analysis, the syn-isomer/anti-isomer ratio was found to be 100/0.

GLC analysis
- Column: Chirasil-Dex CB 0.25 mm×25 m (product of CHROMPACK)
- Injection temperature: 200° C.
- Column temperature: fixed at 150° C.
- Detection temperature: 250° C.

TABLE 2

$$R^1O\text{-}\underset{(5) \text{ or } (9)}{\text{[dioxane ring]}}\text{-COOH} \xrightarrow{A}$$

$$R^1O\text{-}\underset{(11)}{\text{[dioxane ring]}}\text{-COO}^-H^+A$$

| Example | R$^1$ | Compound | Amine (A) | Yield | Syn/Anti |
|---|---|---|---|---|---|
| 12 | (C$_6$H$_5$)$_3$C | 11a | (C$_6$H$_{11}$)NH$_2$ | 83.9 | 99.8/0.2 |
| 13 | (C$_6$H$_5$)$_3$C | 11b | (CH$_3$)$_3$CNH$_2$ | 51.0 | 99.6/0.4 |
| 14 | (C$_6$H$_5$)$_3$C | 11c | (S)-C$_6$H$_5$CH(CH$_3$)NH$_2$ | 80.2 | 100/0.0 |
| 15 | TBDMS | 11d | (C$_6$H$_{11}$)NH$_2$ | 82.7 | 99.4/0.6 |
| 16 | TBDMS | 11e | (CH$_3$)$_3$CNH$_2$ | 77.7 | 99.8/0.2 |
| 17 | TBDMS | 11f | (S)-C$_6$H$_5$CH(CH$_3$)NH$_2$ | 76.5 | 99.8/0.2 |
| 18 | CH$_3$CO | 11g | (C$_6$H$_{11}$)NH$_2$ | 85.2 | 99.8/0.2 |
| 19 | CH$_3$CO | 11h | (CH$_3$)$_3$CNH$_2$ | 88.8 | 99.8/0.2 |
| 20 | CH$_3$CO | 11i | (S)-C$_6$H$_5$CH(CH$_3$)NH$_2$ | 86.9 | 100/0.0 |

(TBDS means tert-butyldimethylsilyl)

As is apparent from Table 2, when reaction was conducted using a primary amine (Examples 12 to 20), the target ammonium (3R,5S)-3,5,6-trihydroxyhexanoate derivative composed of the syn-isomer at a ratio as high as 99.4% or greater was obtained in a high yield.

In Synthesis Example 2(3) and Synthesis of Example 3(2), hydrolysis of methyl (3R,5S)-6-triphenylmethyloxy-3,5-O-isopropylidene-3,5-dihydroxyhexanoate and hydrolysis of methyl (3R,5S)-6-tert-butyldimethylsilyloxy-3,5-O-isopropylidene-3,5-dihydroxyhexanoate were conducted, respectively using sodium hydroxide so that the corresponding sodium salt was formed in each reaction system. As is apparent from Synthesis Example 2(3) and Synthesis Example 3(2), the sodium salt was soluble in water because of high aqueous solubility so that it was utterly difficult to obtain it as crystals.

As described above, in the present invention, use of an alkyl or aralkyl-containing primary amine, alicyclic primary amine or alicyclic secondary amine is very useful for completion of the present reaction.

According to the invention, the ammonium (3R,5S)-3,5,6-trihydroxyhexanoate derivative, which is useful as an intermediate for the synthesis of an HMG-CoA reductase inhibitor, is stable and improved much in chemical selectivity and chemical purity. By crystallization, the derivative can be conveniently and efficiently obtained with high selectivity to its syn-isomer.

While the invention has been described in detail and with reference to specific embodiments thereof, it will be apparent to one skilled in the art that various changes and modifications can be made therein without departing from the spirit and scope thereof.

This application is based on Japanese patent applications No. 2000-252907 filed on Aug. 23, 2000, the entire contents of which incorporated herein by reference.

What is claimed is:

1. An ammonium (3R,5S)-3,5,6-trihydroxyhexanoate compound represented by the following formula (I):

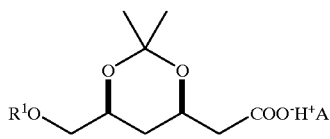

(I)

wherein $R^1$ represents a benzyl group which may have a substituent, a triphenylmethyl group which may have a substituent, an organosilyl group or a $C_{1-5}$ acyl group; and A represents at least one amine selected from the group consisting of a primary amine represented by the following formula (IIIa):

(IIIa)

wherein $R^2$ represents a $C_{1-7}$ alkyl group or a $C_{5-7}$ alicyclic group, a primary benzylamine represented by the following formula (IIIb):

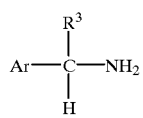

(IIIb)

wherein $R^3$ represents a hydrogen atom, a methyl group or a hydroxymethyl group and Ar represents a phenyl group which may have a substituent, a secondary amine represented by the following formula (IIIc):

(IIIc)

wherein $R^4$ and $R^5$ are same or different and each independently represents a $C_{5-7}$ alicyclic group, cinchamidine, cinchotine, cinchonamine, cinchonidine and cinchonine.

2. An ammonium (3R,5S)-3,5,6-trihydroxyhexanoate according to claim 1, wherein a ratio of the syn-isomer to the anti-isomer falls within a range of 99.0/1 to 100/0.

3. A process for producing an ammonium (3R,5S)-3,5,6-trihydroxyhexanoate in the form of crystals, which comprises causing the amine (A) as claimed in claim 1 to react with a (3R,5S)-3,5,6-trihydroxyhexanoic acid represented by the following formula (II):

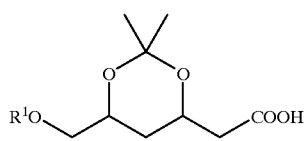

(II)

wherein $R^1$ represents a benzyl group which may have a substituent, a triphenylmethyl group which may have a substituent, an organosilyl group or a $C_{1-5}$ acyl group.

4. A process for producing a high-purity ammonium (3R,5S)-3,5,6-trihydroxyhexanoate in the form of crystals, which comprises causing the amine (A) as claimed in claim 1 to react with the (3R,5S)-3,5,6-trihydroxyhexanoic acid represented by the following formula (II):

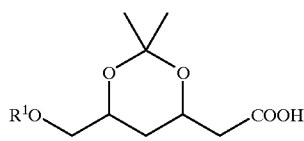

(II)

wherein $R^3$ represents a benzyl group which may have a substituent, a triphenylmethyl group which may have a substituent, an organosilyl group or a $C_{1-5}$ acyl group, and followed by purification of the resulting ammonium (3R,5S)-3,5,6-trihydroxyhexanoate compound by crystallization.

* * * * *